(12) United States Patent
Kalns et al.

(10) Patent No.: US 8,442,808 B2
(45) Date of Patent: May 14, 2013

(54) METHOD OF GUIDING A PHYSICAL TRAINING PROGRAM USING BIOMARKERS OF FATIGUE

(75) Inventors: John E. Kalns, San Antonio, TX (US); Darren J. Michael, San Antonio, TX (US)

(73) Assignee: Hyperion Biotechnology, San Antonio, TX (US)

( * ) Notice: Subject to any disclaimer, the term of this patent is extended or adjusted under 35 U.S.C. 154(b) by 0 days.

(21) Appl. No.: 12/879,551

(22) Filed: Sep. 10, 2010

(65) Prior Publication Data

US 2011/0077472 A1 Mar. 31, 2011

Related U.S. Application Data

(60) Provisional application No. 61/241,519, filed on Sep. 11, 2009.

(51) Int. Cl.
*G06F 7/60* (2006.01)

(52) U.S. Cl.
USPC .......................................................... 703/2

(58) Field of Classification Search ........................ None
See application file for complete search history.

(56) References Cited

PUBLICATIONS

Van Dongen et al. (Aviation, Space, and Environmental Medicine, 2004, vol. 75, No. 3, Section II, p. A15-A36).*
Michael et al. (Accident Analysis and Prevention, 2012, 45S: 68-73).*
Kim and Maeda "Structures of Two HaeIII-Type Genes in the Human Salivary Proline-Rich Protein Multigene Family" *The Journal of Biological Chemistry* 261(15):6712-6718 (1986).
Minaguchi and Bennick "Genetics of Human Salivary Proteins" *J. Dent Res.* 68(1):2-15 (1989).
Carlson "Salivary Proline-Rich Proteins: Biochemistry, Molecular Biology, and Regulation of Expression" *Critical Reviews in Oral Biology and Medicine* 4(¾):495-502 (1993).
Azen "Genetics of Salivary Protein Polymorphisms" *Critical Reviews in Oral Biology and Medicine* 4(¾):479-485 (1993).
Messana et al. "Trafficking and Postsecretory Events Responsible for the Formation of Secreted Human Salivary Peptides" *Molecular & Cellular Proteomics* 7:911-926 (2008).
Abe et al. "The Effects of Epinephrine, Norepinephrine, and Phenylephrine on the Types of Proteins Secreted by Rat Salivary Glands" *J Dent Res* 59(10):1627-1634 (1980).
Akerstedt. "Consensus Statement: Fatigue and Accidents in Transport Operations" *J Sleep Res* 9:395 (2000).
Ament and Verkerke. "Exercise and Fatigue" *Sports Med* 39(5):389-422 (2009).
Amsterdam et al. "Dynamic Changes in the Ultrastructure of the Acinar Cell of the Rat Parotid Gland During the Secretory Cycle" *The Journal of Cell Biology* 41:753-773 (1969).
Caldwell et al. "Fatigue Countermeasures in Aviation" *Aviat Space Environ Med* 80:29-59 (2009).
Campese et al. "Concentration and Fate of Histatins and Acidic Proline-Rich Proteins in the Oral Environment" *Arch Oral Biol* 54(4):345-353 (2009).
Cannon et al. "Increased Interleukin 1β in Human Skeletal Muscle After Exercise" *Am J Physiol* 257:R451-R455 (1989).
Dorian et al. "Phychomotor Vigilance Performance: Neurocognitive Assay Sensitive to Sleep Loss" *Sleep Deprivation: Clinical Issues, Pharmacolody, and Sleep Loss Effects*. Marcel Dekker, New York, Chapter 4, pp. 39-70 (2005).
Garrett and Thulin. "Changes in Parotid Acinar Cells Accompanying Salivary Secretion in Rats on Sympathetic or Parasympathetic Nerve Stimulation" *Cell Tiss Res* 159:179-193 (1975).
Garrett et al. "The Proper Role of Nerves in Salivary Secretion: A Review" *J Dent Res* 66:387-397 (1987).
Granger et al. "Salivary α-Amylase in Biobehavioral Research" *Ann NY Acad Sci* 1098:122-144 (2007).
Hardt et al. "Toward Defining the Human Parotid Gland Salivary Proteome and Peptidome: Identification and Characterization Using 2D SDS-PAGE, Ultrafiltration, HPLC, and Mass Spectrometry" *Biochemistry* 44:2885-2899 (2005).
Harger-Domitrovich et al. "Exogenous Carbohydrate Spares Muscle Glycogen in Men and Women During 10 h of Exercise" *Medicine & Science in Sports & Exercise* 39(12):2171-2179 (2007).
Helmerhorst and Oppenheim. "Saliva: a Dynamic Proteome" *J Dent Res* 86(8):680-693 (2007).
Johnson and Cortez. "Chronic Treatment with Beta Adrenergic Agonists and Antagonists Alters the Composition of Proteins in Rat Parotid Saliva" *J Dent Res* 67(8):1103-1108 (1988).
Johnson et al. "Regulation of Salivary Proteins" *J Dent Res* 66(2):576-582 (1987).
Khaustova et al. "Noninvasive Biochemical Monitoring of Physiological Stress by Fourier Transformation Infrared Saliva Spectroscopy" *Analyst* 135:3183-3192 (2010).
Klein and Corwin. "Seeing the Unexpected: How Sex Differences in Stress Responses May Provide a New Perspective on the Manifestation of Psychiatric Disorders" *Current Psychiatry Reports* 4:441-448 (2002).
Nederfors et al. "Effects of the β-Adrenoceptor Antagonists Atenolol and Propranolol on Human Parotid and Submandibular-Sublingual Salivary Secretion" *J Dent Res* 73(1):5-10 (1994).
Proctor and Carpenter. "Regulation of Salivary Gland Function by Autonomic Nerves" *Autonomic Neuroscience: Basic and Clinical* 133:3-18 (2007).
Van Dongen. "Comparison of Mathematical Model Predictions to Experimental Data of Fatigue and Performance" *Aviat Space Environ Med* 75(3, Suppl.):A15-36 (2004).
Yu et al. "Studies on Peptide Acetylation for Stable-Isotope Labeling After 1-D PAGE Separation in Quantitative Proteomics" *Proteomics* 4:3112-3120 (2004).

(Continued)

*Primary Examiner* — Pablo S Whaley
(74) *Attorney, Agent, or Firm* — Myers Bigel Sibley & Sajovec, P.A.

(57) ABSTRACT

The present invention provides methods and compositions for identifying a subject in a fatigued state, a subject recovering from a fatigued state and/or a subject having an increased likelihood of performing a physical activity at a sufficient level by detecting and/or quantitating, in a sample from the subject, one or more biomarkers associated with fatigue and/or physical performance capability.

2 Claims, 15 Drawing Sheets

PUBLICATIONS

Abe and Dawes. "The Effects of Electrical and Pharmacological Stimulation on the Types of Proteins Secreted by Rat Parotid and Submandibular Glands" *Archives of Oral Biology* 23(5):367-372 (1978).

Borg. "Psychophysical Bases of Perceived Exertion" *Medicine and Science in Sports and Exercise* 14(5):377-381 (1982).

Cannon and Kluger. "Endogenous Pyrogen Activity in Human Plasma After Exercise" *Science* 220(4597):617-619 (1983) (Abstract only).

Johnson. "Changes in Rat Parotid Salivary Proteins Associated with Liquid Diet-Induced Gland Atrophy and Isoproterenol-Induced Gland Enlargement" *Archives of Oral Biology* 29(3):215-221 (1984).

Nederfors et al. "Effects of the Adrenoceptor Antagonists Atenolol and Propranolol on Human Parotid and Submandibular-Sublingual Salivary Secretion" *Journal of Dental Research* 73(1):5-10 (1994).

Purvis et al. "Physiological and Psychological Fatigue in Extreme Conditions: Overtraining and Elite Athletes" *PM&R* 2(5):442-450 (2010).

Borg "Psychophysical Bases of Perceived Exertion" *Medicine and Science in Sports and Exercise* 14(5):377-381 (1982).

Foster et al. "Effect of Pacing Strategy on Cycle Time Trial Performance" *Medicine and Science in Sports and Exercise* 25(3):383-388 (1993).

Kalns et al. "Predicting Success in the Tactical Air Combat Party Training Pipeline" *Military Medicine* 176:431-437 (2011).

Palmer et al. "Effects of Steady-State Versus Stochastic Exercise on Subsequent Cycling Performance" *Med Sci Sports Exerc* 29(5):684-687 (1997).

Pollock et al. " The Recommended Quantity and Quality of Exercise for Developing and Maintaining Cardiorespiratory and Muscular Fitness, and Flexibility in Healthy Adults" *Med Sci Sports Exerc* 30(6):975-991 (1998).

Robinson et al. "Influence of Fatigue on the Efficiency of Men During Exhausting Runs" *J Appl Physiol* 12(2):197-201 (1958).

Quinn "Rating of Perceived Exertion Scale" (Mar. 29, 2004).

* cited by examiner

Fig. 10 cont.

Data Analysis:
Intact Formula (Neutral): $C_{32}H_{45}N_9O_9$
Intact m/z (M+H)⁺: 700.3410
Theoretical m/z: 700.3413
Error: -0.410 ppm Peptide Sequence: AcetylG-G-H-P-P-P-P Matching Fragment Ions:

| Ion Fragment ID | Observed Mass (Da) | Theoretical Mass (Da) | Mass Error (Da) | Mass Error (PPM) | Delta M |
|---|---|---|---|---|---|
| B3 | 4 | 293.1197 | 293.113 | -.0018 | -5.9874 | -- |
|  | 5 | 293.1125 |  | NaN | .1466 |  |
| B4 | 19 | 390.162 | 390.166 | -.0032 | -8.2298 | -- |
|  | 20 | 390.1653 |  | NaN | -.0153 |  |
| B5 | 38 | 487.2177 | 487.218 | -.0003 | -.5603 | -- |
| B6 | 69 | 584.2793 | 584.271 | -.0004 | -.6007 | -- |
| Y2 | 1 | 212.1161 | 212.118 | -.002 | -9.2157 | -- |
| Y3 | 8 | 309.1889 | 309.171 | -.003 | -6.4269 | -- |
| Y4 | 24 | 406.2215 | 406.224 | -.0022 | -5.3788 | -- |
| Y5 | 53 | 543.2803 | 543.283 | -.0023 | -4.2372 | -- |
| Y6 | 71 | 600.3018 | 600.304 | -.0023 | -3.7748 | -- |

Data Analysis:
Intact Formula (Neutral): $C_{33}H_{55}N_7O_{13}$
*Intact m/z (M+H)$^+$: 758.3934*
*Theoretical m/z: 758.3931*
*Error: 0.491 ppm*

*Peptide Sequence:* AcetylE-S-P-S-L-L-A
(Note: Leu could also be Ile, we can't determine this using mass spectrometry)

*Matching Fragment Ions:*

Fig. 11

Proline-rich Salivary Genes Giving Rise to Fatigue Biomarker Peptides #1 and 2.
PRH1/PRH2 Genes Products MLLILLSVALLAFSSAQDLNEDVSQEDVPLVISDGGDSEQFLDEERQGPPLGGQQSQPSAGDG
NQDDGPQQGPPQQGGQQQQGPPPPQGKPQGPPQQGGHPPPPQGRPQGPPQQGGHPRPPRGR
PQGPPQQGGHQQGPPPPPPGKPQGPPPQGGRPQGPPQGQSPQ

| Product | Position | Length |
|---|---|---|
| Primary Translation Product | 1-166 | 166 aa |
| Signal Peptide | 1-16 | 16 aa |
| Salivary Acidic Proteins 1 & 2 | 17-166 | 150 aa |
| Salivary Acidic Proteins 3 & 4 | 17-122 | 104 aa |
| Peptide P-C | 123-166 | 44 aa |
| Biomarker Peptide #1 | 98-104 | 7 aa |

\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*

PRB1 Gene Products

MLLILLSVALLALSSAQNLNEDVSQEESPSLIAGNPQGPSPQGGNKPQGPPPPPGKPQGPPPQG
GNKPQGPPPPGKPQGPPPQGDKSRSPRSPPGKPQGPPPQGGNQPQGPPPPPGKPQGPPPQGGN
KPQGPPPPGKPQGPPPQGDKSQSPRSPPGKPQGPPPQGGNQPQGPPPPPGKPQGPPPQGGNKP
QGPPPPGKPQGPPPQGDKSQSPRSPPGKPQGPPPQGGNQPQGPPPPPGKPQGPPQQGGNRPQG
PPPPGKPQGPPPQGDKSRSPQSPPGKPQGPPPQGGNQPQGPPPPPGKPQGPPPQGGNKPQGPPP
PGKPQGPPAQGGSKSQSARAPPGKPQGPPQQEGNNPQGPPPPAGGNPQQPQAPPAGQPQGPP
RPPQGGRPSRPPQ

| Product | Position | Length |
|---|---|---|
| Primary Translation Product | 1-376 | 376 aa |
| Signal Peptide | 1-16 | 16 aa |
| Basic Salivary Proline-rich Protein 1 | 17-166 | 150 aa |
| Proline-rich Peptide II-2 | 17-91 | 75 aa |
| Basic Peptide IB-6 | 275-392 | 118 aa |
| Peptide P-H | 337-392 | 56 aa |
| Biomarker Peptide #2 | 27-33 | 7 aa |

PRB2 Gene Products

MLLILLSVALLALSSAQNLNEDVSQEESPSLIAGNPQGAPPQGGNKPQGPPSPPGKPQGPPPQ
GGNQPQGPPPPPGKPQGPPPQGGNKPQGPPPPGKPQGPPPQGDKSRSPRSPPGKPQGPPPQGG
NQPQGPPPPPGKPQGPPPQGGNKPQGPPPPGKPQGPPPQGDNKSRSSRSPPGKPQGPPPQGGN
QPQGPPPPPGKPQGPPPQGGNKPQGPPPPGKPQGPPPQGDNKSQSARSPPGKPQGPPPQGGNQ
PQGPPPPPGKPQGPPPQGGNKSQGPPPPGKPQGPPPQGGSKSRSSRSPPGKPQGPPPQGGNQPQ
GPPPPPGKPQGPPPQGGNKPQGPPPPGKPQGPPPQGGSKSRSARSPPGKPQGPPQQEGNNPQG
PPPPAGGNPQQPQAPPAGQPQGPPRPPQGGRPSRPPQ

| Product | Position | Length |
|---|---|---|
| Primary Translation Product | 1-416 | 416 aa |
| Signal Peptide | 1-16 | 16 aa |
| Basic Salivary Proline-rich Protein 2 | 17-416 | 400 aa |
| Basic Proline-rich Peptide IB-7 | 113-171 | 59 aa |
| Basic Proline-rich Peptide IB-8c | 299-359 | 61 aa |
| Basic Pline-rich Peptide IB-4H | 361-416 | 56 aa |
| Biomarker Peptide #2 | 27-33 | 7 aa |

*******************************************************************

METHOD OF GUIDING A PHYSICAL TRAINING PROGRAM USING BIOMARKERS OF FATIGUE

STATEMENT OF PRIORITY

This application claims the benefit, under 35 U.S.C. §119 (e), of U.S. Provisional Application Ser. No. 61/241,519, filed Sep. 11, 2009, the entire contents of which are incorporated by reference herein.

STATEMENT OF GOVERNMENT SUPPORT

Aspects of this invention were made with government support provided under United States Army contract W911SR-07-C-0006; United States Air Force contracts FA8902-05-C-0005, FA8900-06-D-0006 Task Order 6 and Task Order 12. The U.S. Government has certain rights in this invention.

FIELD OF THE INVENTION

The present invention relates to biomarkers and methods of their use in identifying fatigue, recovery from fatigue and/or physical performance capability in a subject.

BACKGROUND OF THE INVENTION

There is great interest in finding methods that can be used to evaluate objectively the physical and cognitive capability of a subject or group of subjects (e.g., military personnel). As one example, an objective, real-time measurement tool would be useful in deciding whether tired troops should be deployed. Other applications include evaluation of shift work strategies, selection for special duties and training.

The present invention fulfills this need by providing methods and compositions for analyzing and/or evaluating a subject's level of fatigue and/or physical performance capability (e.g., fitness) by detecting and/or measuring biomarkers associated with fatigue, fitness and physical performance capacity in one or more, samples from the subject.

BRIEF DESCRIPTION OF THE DRAWINGS

FIG. 11. Proline-rich salivary genes giving rise to fatigue biomarker peptides #1 and 2. PRH1/PRH2 Gene Products:

Figure 1:
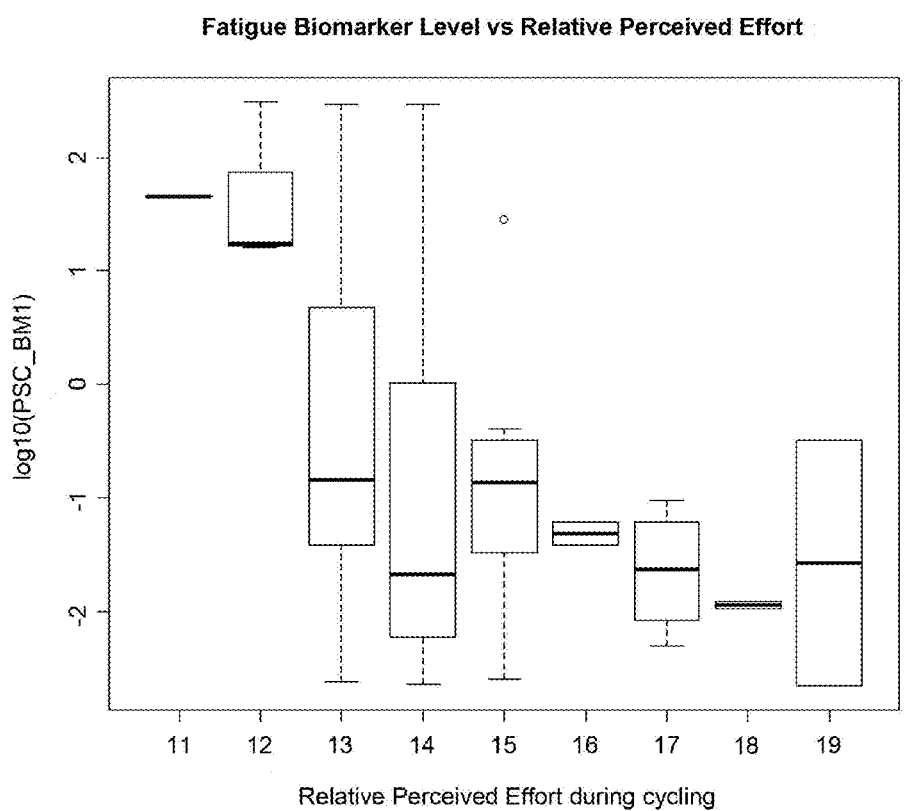
FIG. 1. Biomarker index level decreases as relative perceived effort increases during repeated periods of cycling. Fatigue biomarker index (FBI) levels were measured using the method described herein. The base 10 logarithm of the fatigue biomarker index level was plotted against the relative perceived effort of cyclists for repeated sessions during a study of endurance exercise lasting ten hours. (Pearson's product-moment correlation, Correlation coefficient: −0.3826043, p-value: 0.002553, alternative hypothesis: true correlation is not equal to 0.)

SEQ ID NO:6; PRB1 Gene Products: SEQ ID NO:7; PRB2 Gene Products: SEQ ID NO:8.

SUMMARY OF THE INVENTION

In one aspect, the present invention provides a method of identifying a subject in a fatigued state following physical activity, comprising: a) measuring, at a first time point prior to performing a physical activity, the amount of each of two peptides, GGHPPPP (SEQ ID NO:1) and ESPSLIA (SEQ ID NO:2), in a first sample from the subject; b) calculating the ratio of the amount of each of the two peptides of (a) to identify a biomarker index for the subject in the absence of a fatigued state; c) measuring, at a subsequent time point after performing a physical activity, the amount of each of the two peptides, GGHPPPP (SEQ ID NO:1) and ESPSLIA (SEQ ID NO:2), in a subsequent sample from the subject; and d) calculating the ratio of the amount of each of the two peptides of (c) to identify a biomarker index for the subject after performing a physical activity, whereby a decrease in the biomarker index of (d) relative to the biomarker index of (b) identifies a subject in a fatigued state following physical activity.

The present invention also provides a method of identifying a subject in a fatigued state, comprising: a) measuring, at a first time point when the subject is in a rested state, the amount of each of two peptides, GGHPPPP (SEQ ID NO:1) and ESPSLIA (SEQ ID NO:2), in a first sample from the subject; b) calculating the ratio of the amount of each of the two peptides of (a) to identify a biomarker index for the subject in a rested state; c) measuring, at a subsequent time point, the amount of each of the two peptides, GGHPPPP (SEQ ID NO:1) and ESPSLIA (SEQ ID NO:2), in a subsequent sample from the subject; and d) calculating the ratio of the amount of each of the two peptides of (c) to identify a biomarker index for the subject at the subsequent time point, whereby a decrease in the biomarker index of (d) relative to the biomarker index of (b) identifies a subject in a fatigued state.

In further aspects, a method is provided herein of identifying an increased level of fatigue in a subject due to physical activity of the subject over time, comprising: a) measuring, at a first time point prior to performing a physical activity, the amount of each of two peptides, GGHPPPP (SEQ ID NO:1) and ESPSLIA (SEQ ID NO:2), in a first sample from the subject; b) calculating the ratio of the amount of each of the two peptides of (a) to identify a biomarker index for the subject in the absence of fatigue due to physical activity; c) measuring, at one or more subsequent time points during the performance of the physical activity and/or after performing a physical activity, the amount of each of two peptides, GGHPPPP (SEQ ID NO:1) and ESPSLIA (SEQ ID NO:2), in one or more subsequent samples from the subject; and d) calculating the ratio of the amount of each of the two peptides of (c) for each subsequent time point to identify one or more biomarker indices for the subject for each subsequent time point during performance of the physical activity and/or after performing a physical activity, whereby a decrease in the one or more biomarker indices of (d) relative to the biomarker index of (b) over time during the performance of the physical activity and/or after performing the physical activity identifies an increased level of fatigue in the subject due to physical activity of the subject over time.

In addition, the present invention provides a method of identifying a decrease in the physical performance capability of a subject over time, comprising: a) measuring, at a first time point the amount of each of two peptides, GGHPPPP (SEQ ID NO:1) and ESPSLIA (SEQ ID NO:2), in a first sample from the subject; b) calculating the ratio of the amount of each of the two peptides of (a) to identify a first biomarker index for the subject at the first time point; c) measuring, at one or more subsequent time points, the amount of each of the two peptides, GGHPPPP (SEQ ID NO:1) and ESPSLIA (SEQ ID NO:2), in one or more subsequent samples from the subject; and d) calculating the ratio of the amount of each of the two peptides of (c) for each subsequent time point to identify one or more biomarker indices for the subject for each subsequent time point, whereby a decrease in the one or more biomarker indices of (d) relative to the first biomarker index of (b) identifies a decrease in the physical performance capability of the subject over time.

Further aspects of the present invention include a method of identifying fatigue in a test subject, comprising: a) measuring the amount of each of two peptides, GGHPPPP (SEQ ID NO:1) and ESPSLIA (SEQ ID NO:2), in a sample from each study subject in a population of study subjects; b) calculating the ratio of the amount of each of the two peptides, of (a) to identify a biomarker index for each study subject; c) establishing a threshold biomarker index for the population of study subjects of (a); d) measuring the amount of each of the two peptides, GGHPPPP (SEQ ID NO:1) and ESPSLIA (SEQ ID NO:2), in a sample from the test subject; and e) calculating the ratio of the amount of each of the two peptides of (d) to identify a biomarker index for the test subject, whereby a biomarker index of the test subject that is lower than the threshold biomarker index of (c) identifies fatigue in the test subject.

The present invention also provides a method of correlating a subject's perceived level of fatigue with a biomarker index, comprising: a) obtaining from the subject a first value of the subject's perceived level of fatigue at a first time point; b) measuring, at the first time point the amount of each of two peptides, GGHPPPP (SEQ ID NO:1) and ESPSLIA (SEQ ID NO:2), in a first sample from the subject; c) calculating the ratio of the amount of each of the two peptides of (b) to identify a first biomarker index for the subject at the first time point; d) obtaining from the subject one or more subsequent values of the subject's perceived level of fatigue at one or more subsequent time points; e) measuring, at the one or more subsequent time points, the amount of each of the two peptides, GGHPPPP (SEQ ID NO:1) and ESPSLIA (SEQ ID NO:2), in one or more subsequent samples from the subject; f) calculating the ratio of the amount of each of the two peptides of (e) for each subsequent time point to identify one or more biomarker indices for the subject for each subsequent time point; and g) correlating the subject's perceived level of fatigue with the biomarker index or indices.

Furthermore, the present invention provides a method of identifying recovery from a fatigued state in a subject, comprising: a) measuring, at a first time point the amount of each of two peptides, GGHPPPP (SEQ ID NO:1) and ESPSLIA (SEQ ID NO:2), in a first sample from the subject when the subject is in a fatigued state or suspected of being in a fatigued state; b) calculating the ratio of the amount of each of the two peptides of (a) to identify a first biomarker index for the subject at the first time point; c) measuring, at one or more later time points, the amount of each of the two peptides, GGHPPPP (SEQ ID NO:1) and ESPSLIA (SEQ ID NO:2), in one or more later samples from the subject; and f) calculating the ratio of the amount of each of the two peptides of (c) for each later time point to identify one or more biomarker indices for each later time point, whereby an increase in the one or more biomarker indices relative to the first biomarker index of (b) identifies recovery from the fatigued state in the subject.

Another aspect of the present invention is a method of identifying recovery from a fatigued state in a test subject, comprising: a) measuring the amount of each of two peptides, GGHPPPP (SEQ ID NO:1) and ESPSLIA (SEQ ID NO:2), in a sample from each study subject in a population of study subjects in a fatigued state; b) calculating the ratio of the amount of each of the two peptides of (a) to identify a biomarker index for each study subject; c) establishing a threshold biomarker index for the population of study subjects of (a); d) measuring the amount of each of the two peptides, GGHPPPP (SEQ ID NO:1) and ESPSLIA (SEQ ID NO:2), in a sample from the test subject; e) calculating the ratio of the amount of each of the two peptides of (d) to identify a biomarker index for the test subject, whereby a biomarker index of the test subject that is lower than the threshold biomarker index of (c) identifies the test subject as having a fatigued state; f) measuring the amount of each of the two peptides, GGHPPPP (SEQ ID NO:1) and ESPSLIA (SEQ ID NO:2), in one or more samples from the test subject at later time points; g) calculating the ratio of the amount of each of the two peptides of (f) to identify one or more biomarker indices for the test subject at the later time points, whereby an increase in the one or more biomarker indices at the later time points relative to the biomarker indices of (e) identifies recovery of the test subject from the fatigued state or diminution of fatigue.

Also provided herein is a method of identifying a test subject having an increased likelihood of performing a physical activity at a sufficient level, comprising: a) measuring the amount of each of two peptides, GGHPPPP (SEQ ID NO:1) and ESPSLIA (SEQ ID NO:2), in a sample from each study subject in a population of study subjects that have performed the physical activity at a sufficient level; b) calculating the ratio of the amount of each of the two peptides of (a) to identify a biomarker index for each study subject; c) establishing a threshold biomarker index for the population of study subjects of (a); d) measuring the amount of each of the two peptides, GGHPPPP (SEQ ID NO:1) and ESPSLIA (SEQ ID NO:2), in a sample from the test subject; and e) calculating the ratio of the amount of each of the two peptides of (d) to identify a biomarker index for the test subject, whereby a biomarker index of the test subject that is equal to or greater than the threshold biomarker index of (c) identifies the test subject as having an increased likelihood of performing the physical activity at a sufficient level.

In other aspects, the present invention provides a method of identifying a test subject having a decreased likelihood of performing a physical activity at a sufficient level, comprising: a) measuring the amount of each of two peptides, GGHPPPP (SEQ ID NO:1) and ESPSLIA (SEQ ID NO:2), in a sample from each study subject in a population of study subjects that have performed the physical activity at a sufficient level; b) calculating the ratio of the amount of each of the two peptides of (a) to identify a biomarker index for each study subject; c) establishing a threshold biomarker index for the population of study subjects of (a); d) measuring the amount of each of the two peptides, GGHPPPP (SEQ ID NO:1) and ESPSLIA (SEQ ID NO:2), in a sample from the test subject; and e) calculating the ratio of the amount of each of the two peptides of (d) to identify a biomarker index for the test subject, whereby a biomarker index of the test subject that is less than the threshold biomarker index of (c) identifies the test subject as having a decreased likelihood of performing the physical activity at a sufficient level.

Further provided herein is a method of identifying a test subject having an increased likelihood of performing a physical activity at a sufficient level, comprising: a) measuring, at a first time point, the amount of each of two peptides, GGHPPPP (SEQ ID NO:1) and ESPSLIA (SEQ ID NO:2), in a first sample from a subject prior to performance of the physical activity at a sufficient level; b) calculating the ratio of the amount of each of the two peptides of (a) to identify a biomarker index for the subject indicative of the subject's ability to perform the physical activity at a sufficient level; c) measuring, at one or more later time points, the amount of each of two peptides, GGHPPPP (SEQ ID NO:1) and ESPSLIA (SEQ ID NO:2), in one or more later samples from the subject prior to performing a physical activity; and d) calculating the ratio of the amount of each of the two peptides of (c) for each of the one or more later time points to identify a biomarker index for each of the one or more later time points, whereby a biomarker index for each of the one or more later time points that is equal to or greater than the biomarker index of (b) identifies the test subject as having an increased likelihood of performing the physical activity at a sufficient level.

Other embodiments of this invention include a method of identifying a test subject having a decreased likelihood of performing a physical activity at a sufficient level, comprising: a) measuring, at a first time point, the amount of each of two peptides, GGHPPPP (SEQ ID NO:1) and ESPSLIA (SEQ ID NO:2), in a first sample from a subject prior to performance of the physical activity at a sufficient level; b) calculating the ratio of the amount of each of the two peptides of (a) to identify a biomarker index for the subject indicative of the subject's ability to perform the physical activity at a sufficient level; c) measuring, at one or more later time points, the amount of each of two peptides, GGHPPPP (SEQ ID NO:1) and ESPSLIA (SEQ ID NO:2), in one or more later samples from the subject prior to performing a physical activity; and d) calculating the ratio of the amount of each of the two peptides of (c) for each of the one or more later time points to identify a biomarker index for each of the one or more later time points, whereby a biomarker index for each of the one or more later time points that is less than the biomarker index of (b) identifies the test subject as having a decreased likelihood of performing the physical activity at a sufficient level.

Additionally provided herein is a method of identifying a decrease in the level of fatigue in a subject due to physical activity of the subject over time, comprising: a) measuring, at a first time point prior to performing a physical activity, the amount of each of two peptides, GGHPPPP (SEQ ID NO:1) and ESPSLIA (SEQ ID NO:2), in a first sample from the subject; b) calculating the ratio of the amount of each of the two peptides of (a) to identify a biomarker index for the subject in the absence of fatigue due to physical activity; c) measuring, at one or more subsequent time points during the performance of the physical activity and/or after performing the physical activity, the amount of each of two peptides, GGHPPPP (SEQ ID NO:1) and ESPSLIA (SEQ ID NO:2), in one or more subsequent samples from the subject; d) calculating the ratio of the amount of each of the two peptides of (c) for each subsequent time point to identify one or more biomarker indices for the subject for each subsequent time point during performance of the physical activity and/or after performing the physical activity, whereby a decrease in the one or more biomarker indices of (d) relative to the biomarker index of (b) over time during the performance of the physical activity and/or after performing the physical activity identifies fatigue in the subject due to physical activity of the subject over time; e) subsequently measuring, after step (d), at one or more later time points during the performance of the physical activity and/or after performing a physical activity, the amount of each of two peptides, GGHPPPP (SEQ ID NO:1) and ESPSLIA (SEQ ID NO:2), in one or more later samples from the subject; and f) calculating the ratio of the amount of each of the two peptides of (e) for each later time point to identify one or more later biomarker indices for the subject for each later time point during performance of the physical activity and/or after performing a physical activity, whereby an increase or a lesser decrease in the one or more later biomarker indices of (f) relative to the biomarker indices of (d) over time during the performance of the physical activity and/or after performing the physical activity identifies a decreased level of fatigue in the subject due to physical activity of the subject over time.

The present invention further provides a method of identifying an improvement in physical performance capability of a subject over time, comprising: a) measuring, at a first time point prior to performing a physical activity, the amount of each of two peptides, GGHPPPP (SEQ ID NO:1) and ESPSLIA (SEQ ID NO:2), in a first sample from the subject; b) calculating the ratio of the amount of each of the two peptides of (a) to identify a biomarker index for the subject in the absence of fatigue due to physical activity; c) measuring, at one or more subsequent time points during the performance of the physical activity and/or after performing the physical activity, the amount of each of two peptides, GGHPPPP (SEQ ID NO:1) and ESPSLIA (SEQ ID NO:2), in one or more subsequent samples from the subject; d) calculating the ratio of the amount of each of the two peptides of (c) for each subsequent time point to identify one or more biomarker indices for the subject for each subsequent time point during performance of the physical activity and/or after performing the physical activity, whereby a decrease in the one or more biomarker indices of (d) relative to the biomarker index of (b) over time during the performance of the physical activity and/or after performing the physical activity identifies fatigue in the subject due to physical activity of the subject over time; e) subsequently measuring, after step (d), at one or more later time points during the performance of the physical activity and/or after performing the physical activity, the amount of each of two peptides, GGHPPPP (SEQ ID NO:1) and ESPSLIA (SEQ ID NO:2), in one or more later samples from the subject; and f) calculating the ratio of the amount of each of the two peptides of (e) for each later time point to identify one or more later biomarker indices for the subject for each later time point during performance of the physical activity and/or after performing a physical activity, whereby an increase or a lesser decrease in the one or more later biomarker indices of (f) relative to the biomarker indices of (d) over time during the performance of the physical activity and/or after performing the physical activity identifies an improvement in physical performance capability over time.

Further aspects of the present invention include an isolated peptide comprising the amino acid sequence GGHPPPP (SEQ ID NO:1), an isolated peptide comprising the amino acid sequence ESPSLIA (SEQ ID NO:2) and a composition comprising either or both of these peptides in a pharmaceutically acceptable carrier.

In addition, the present invention provides a method of identifying a substance that binds a peptide of this invention, comprising contacting the peptide with a test compound under conditions whereby binding between the peptide and the test compound can be detected; and detecting binding between the polypeptide and the test compound.

Also provided herein is method of identifying a compound that modulates the activity of a peptide of this invention, comprising contacting the peptide with a test compound under conditions whereby modulation of the activity of the peptide can be detected; and detecting modulation of the activity of the peptide.

Further provided is a method of identifying a substance having the ability to inhibit or enhance the binding activity of a peptide of this invention, comprising contacting the substance with the peptide under conditions whereby binding can occur and detecting a decrease or increase in the amount of binding in the presence of the substance as compared to a control amount of binding in the absence of the substance, thereby identifying a substance having the ability to inhibit or enhance the binding activity of the peptide.

Additionally, the present invention provides a method of identifying immunomodulating activity in a peptide of this invention, comprising employing the peptide or peptides in an assay for immunomodulating activity and detecting immunomodulating activity in the presence of the peptide as compared to a control, thereby identifying immunomodulating activity in the peptide.

Furthermore, a method is provided herein of identifying antimicrobial activity in a peptide of this invention, comprising employing the peptide in an assay for antimicrobial activity and detecting antimicrobial activity in the presence of the peptide or peptides as compared to a control, thereby identifying antimicrobial activity in the peptide.

DETAILED DESCRIPTION OF THE INVENTION

As used herein, "a" or "an" or "the" can mean one or more than one. For example, "a" cell can mean one cell or a plurality of cells.

Also as used herein, "and/or" refers to and encompasses any and/or all possible combinations of one or more of the associated listed items, as well as the lack of and/or combinations when interpreted in the alternative ("or").

Furthermore, the term "about" as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations and variations thereof.

The present invention is based on the unexpected discovery of biomarkers (e.g., peptides) associated with fatigue, recovery from fatigue and/or physical performance capability (e.g., fitness) in a subject and the ability to detect, measure and/or monitor fatigue, recovery from fatigue and/or physical performance capability of the subject by detecting, measuring and/or monitoring these biomarkers in one or more samples from the subject.

Identification Methods

In one aspect, the present invention provides a method of identifying a subject in a fatigued state following physical activity, comprising: a) measuring, at a first time point prior to performing a physical activity, the amount of each of two peptides, GGHPPPP (SEQ ID NO:1) and ESPSLIA (SEQ ID NO:2), in a first sample from the subject; b) calculating the ratio of the amount of each of the two peptides of (a) to identify a biomarker index for the subject in the absence of a fatigued state; c) measuring, at a subsequent time point after performing a physical activity, the amount of each of the two peptides, GGHPPPP (SEQ ID NO:1) and ESPSLIA (SEQ ID NO:2), in a subsequent sample from the subject; and d) calculating the ratio of the amount of each of the two peptides of (c) to identify a biomarker index for the subject after performing a physical activity, whereby a decrease in the biomarker index of (d) relative to the biomarker index of (b) identifies a subject in a fatigued state following physical activity.

The present invention also provides a method of identifying a subject in a fatigued state, comprising: a) measuring, at a first time point when the subject is in a rested state, the amount of each of two peptides, GGHPPPP (SEQ ID NO:1) and ESPSLIA (SEQ ID NO:2), in a first sample from the subject; b) calculating the ratio of the amount of each of the two peptides of (a) to identify a biomarker index for the subject in a rested state; c) measuring, at a subsequent time point, the amount of each of the two peptides, GGHPPPP (SEQ ID NO:1) and ESPSLIA (SEQ ID NO:2), in a subsequent sample from the subject; and d) calculating the ratio of the amount of each of the two peptides of (c) to identify a biomarker index for the subject at the subsequent time point, whereby a decrease in the biomarker index of (d) relative to the biomarker index of (b) identifies a subject in a fatigued state.

In further aspects, a method is provided herein of identifying an increased level of fatigue in a subject due to physical activity of the subject over time, comprising: a) measuring, at a first time point prior to performing a physical activity, the amount of each of two peptides, GGHPPPP (SEQ ID NO:1) and ESPSLIA (SEQ ID NO:2), in a first sample from the subject; b) calculating the ratio of the amount of each of the two peptides of (a) to identify a biomarker index for the subject in the absence of fatigue due to physical activity; c) measuring, at one or more subsequent time points during the performance of the physical activity and/or after performing a physical activity, the amount of each of two peptides, GGHPPPP (SEQ ID NO:1) and ESPSLIA (SEQ ID NO:2), in one or more subsequent samples from the subject; and d) calculating the ratio of the amount of each of the two peptides of (c) for each subsequent time point to identify one or more biomarker indices for the subject for each subsequent time point during performance of the physical activity and/or after performing a physical activity, whereby a decrease in the one or more biomarker indices of (d) relative to the biomarker index of (b) over time during the performance of the physical activity and/or after performing the physical activity identifies an increased level of fatigue in the subject due to physical activity of the subject over time.

In addition, the present invention provides a method of identifying a decrease in the physical performance capability of a subject over time, comprising: a) measuring, at a first time point the amount of each of two peptides, GGHPPPP (SEQ ID NO:1) and ESPSLIA (SEQ ID NO:2), in a first sample from the subject; b) calculating the ratio of the amount of each of the two peptides of (a) to identify a first biomarker index for the subject at the first time point; c) measuring, at one or more subsequent time points, the amount of each of the two peptides, GGHPPPP (SEQ ID NO:1) and ESPSLIA (SEQ ID NO:2), in one or more subsequent samples from the subject; and d) calculating the ratio of the amount of each of the two peptides of (c) for each subsequent time point to identify one or more biomarker indices for the subject for each subsequent time point, whereby a decrease in the one or more biomarker indices of (d) relative to the first biomarker index of (b) identifies a decrease in the physical performance capability of the subject over time.

Further aspects of the present invention include a method of identifying fatigue in a test subject, comprising: a) measuring the amount of each of two peptides, GGHPPPP (SEQ ID NO:1) and ESPSLIA (SEQ ID NO:2), in a sample from each study subject in a population of study subjects; b) calculating the ratio of the amount of each of the two peptides of (a) to identify a biomarker index for each study subject; c) establishing a threshold biomarker index for the population of study subjects of (a); d) measuring the amount of each of the two peptides, GGHPPPP (SEQ ID NO:1) and ESPSLIA (SEQ ID NO:2), in a sample from the test subject; and e) calculating the ratio of the amount of each of the two peptides of (d) to identify a biomarker index for the test subject, whereby a biomarker index of the test subject that is lower than the threshold biomarker index of (c) identifies fatigue in the test subject.

The present invention also provides a method of correlating a subject's perceived level of fatigue with a biomarker index, comprising: a) obtaining from the subject a first value of the subject's perceived level of fatigue at a first time point; b) measuring, at the first time point the amount of each of two peptides, GGHPPPP (SEQ ID NO:1) and ESPSLIA (SEQ ID NO:2), in a first sample from the subject; c) calculating the ratio of the amount of each of the two peptides of (b) to identify a first biomarker index for the subject at the first time point; d) obtaining from the subject one or more subsequent values of the subject's perceived level of fatigue at one or more subsequent time points; e) measuring, at the one or more subsequent time points, the amount of each of the two peptides, GGHPPPP (SEQ ID NO:1) and ESPSLIA (SEQ ID NO:2), in one or more subsequent samples from the subject; f) calculating the ratio of the amount of each of the two peptides of (e) for each subsequent time point to identify one or more biomarker indices for the subject for each subsequent time point; and g) correlating the subject's perceived level of fatigue with the biomarker index or indices.

Furthermore, the present invention provides a method of identifying recovery from a fatigued state in a subject, comprising: a) measuring, at a first time point the amount of each of two peptides, GGHPPPP (SEQ ID NO:1) and ESPSLIA (SEQ ID NO:2), in a first sample from the subject when the subject is in a fatigued state or suspected of being in a fatigued state; b) calculating the ratio of the amount of each of the two peptides of (a) to identify a first biomarker index for the subject at the first time point; c) measuring, at one or more later time points, the amount of each of the two peptides, GGHPPPP and ESPSLIA, in one or more later samples from the subject; and f) calculating the ratio of the amount of each of the two peptides of (c) for each later time point to identify one or more biomarker indices for each later time point, whereby an increase in the one or more biomarker indices relative to the first biomarker index of (b) identifies recovery from the fatigued state in the subject.

Another aspect of the present invention is a method of identifying recovery from a fatigued state in a test subject, comprising: a) measuring the amount of each of two peptides, GGHPPPP (SEQ ID NO:1) and ESPSLIA (SEQ ID NO:2), in a sample from each study subject in a population of study subjects in a fatigued state; b) calculating the ratio of the amount of each of the two peptides of (a) to identify a biomarker index for each study subject; c) establishing a threshold biomarker index for the population of study subjects of (a); d) measuring the amount of each of the two peptides, GGHPPPP (SEQ ID NO:1) and ESPSLIA (SEQ ID NO:2), in a sample from the test subject; e) calculating the ratio of the amount of each of the two peptides of (d) to identify a biomarker index for the test subject, whereby a biomarker index of the test subject that is lower than the threshold biomarker index of (c) identifies the test subject as having a fatigued state; f) measuring the amount of each of the two peptides, GGHPPPP (SEQ ID NO:1) and ESPSLIA (SEQ ID NO:2), in one or more samples from the test subject at later time points; g) calculating the ratio of the amount of each of the two peptides of (f) to identify one or more biomarker indices for the test subject at the later time points, whereby an increase in the one or more biomarker indices at the later time points relative to the biomarker indices of (e) identifies recovery of the test subject from the fatigued state. In some embodiments, this method can further comprise the step of measuring the amount of each of the two peptides, GGHPPPP (SEQ ID NO:1) and ESPSLIA (SEQ ID NO:2), in a pre-fatigue sample from the subject and calculating the ratio of the amount of each of the two peptides to identify a pre-fatigue biomarker index for the subject.

Also provided herein is a method of identifying a test subject having an increased likelihood of performing a physical activity at a sufficient level, comprising: a) measuring the amount of each of two peptides, GGHPPPP (SEQ ID NO:1) and ESPSLIA (SEQ ID NO:2), in a sample from each study subject in a population of study subjects that have performed the physical activity at a sufficient level; b) calculating the ratio of the amount of each of the two peptides of (a) to identify a biomarker index for each study subject; c) establishing a threshold biomarker index for the population of study subjects of (a); d) measuring the amount of each of the two peptides, GGHPPPP (SEQ ID NO:1) and ESPSLIA (SEQ ID NO:2), in a sample from the test subject; and e) calculating the ratio of the amount of each of the two peptides of (d) to identify a biomarker index for the test subject, whereby a biomarker index of the test subject that is equal to or greater than the threshold biomarker index of (c) identifies the test subject as having an increased likelihood of performing the physical activity at a sufficient level.

In other aspects, the present invention provides a method of identifying a test subject having a decreased likelihood of performing a physical activity at a sufficient level, comprising: a) measuring the amount of each of two peptides, GGHPPPP (SEQ ID NO:1) and ESPSLIA (SEQ ID NO:2), in a sample from each study subject in a population of study subjects that have performed the physical activity at a sufficient level; b) calculating the ratio of the amount of each of the two peptides of (a) to identify a biomarker index for each study subject; c) establishing a threshold biomarker index for the population of study subjects of (a); d) measuring the amount of each of the two peptides, GGHPPPP (SEQ ID NO:1) and ESPSLIA (SEQ ID NO:2), in a sample from the test subject; and e) calculating the ratio of the amount of each of the two peptides of (d) to identify a biomarker index for the test subject, whereby a biomarker index of the test subject that is less than the threshold biomarker index of (c) identifies the test subject as having a decreased likelihood of performing the physical activity at a sufficient level.

Further provided herein is a method of identifying a test subject having an increased likelihood of performing a physical activity at a sufficient level, comprising: a) measuring, at a first time point, the amount of each of two peptides, GGHPPPP (SEQ ID NO:1) and ESPSLIA (SEQ ID NO:2), in a first sample from a subject prior to performance of the physical activity at a sufficient level; b) calculating the ratio of the amount of each of the two peptides of (a) to identify a biomarker index for the subject indicative of the subject's ability to perform the physical activity at a sufficient level; c) measuring, at one or more later time points, the amount of each of two peptides, GGHPPPP (SEQ ID NO:1) and ESPSLIA (SEQ ID NO:2), in one or more later samples from the subject prior to performing the physical activity; and d) calculating the ratio of the amount of each of the two peptides of (c) for each of the one or more later time points to identify a biomarker index for each of the one or more later time points, whereby a biomarker index for each of the one or more later time points that is equal to or greater than the biomarker index of (b) identifies the test subject as having an increased likelihood of performing the physical activity at a sufficient level.

Other embodiments of this invention include a method of identifying a test subject having a decreased likelihood of performing a physical activity at a sufficient level, comprising: a) measuring, at a first time point, the amount of each of two peptides, GGHPPPP (SEQ ID NO:1) and ESPSLIA (SEQ ID NO:2), in a first sample from a subject prior to performance of the physical activity at a sufficient level; b) calculating the ratio of the amount of each of the two peptides of (a) to identify a biomarker index for the subject indicative of the subject's ability to perform the physical activity at a sufficient level; c) measuring, at one or more later time points, the amount of each of two peptides, GGHPPPP (SEQ ID NO:1) and ESPSLIA (SEQ ID NO:2), in one or more later samples from the subject prior to performing a physical activity; and d) calculating the ratio of the amount of each of the two peptides of (c) for each of the one or more later time points to identify a biomarker index for each of the one or more later time points, whereby a biomarker index for each of the one or more later time points that is less than the biomarker index of (b) identifies the test subject as having a decreased likelihood of performing the physical activity at a sufficient level.

Additionally provided herein is a method of identifying a decrease in the level of fatigue in a subject due to physical activity of the subject over time, comprising: a) measuring, at a first time point prior to performing a physical activity, the amount of each of two peptides, GGHPPPP (SEQ ID NO:1) and ESPSLIA (SEQ ID NO:2), in a first sample from the subject; b) calculating the ratio of the amount of each of the two peptides of (a) to identify a biomarker index for the subject in the absence of fatigue due to physical activity; c) measuring, at one or more subsequent time points during the performance of the physical activity and/or after performing the physical activity, the amount of each of two peptides, GGHPPPP (SEQ ID NO:1) and ESPSLIA (SEQ ID NO:2) in one or more subsequent samples from the subject; d) calculating the ratio of the amount of each of the two peptides of (c) for each subsequent time point to identify one or more biomarker indices for the subject for each subsequent time point during performance of the physical activity and/or after performing the physical activity, whereby a decrease in the one or more biomarker indices of (d) relative to the biomarker index of (b) over time during the performance of the physical activity and/or after performing the physical activity identifies fatigue (e.g., a level of fatigue) in the subject due to physical activity of the subject over time; e) subsequently measuring, after step (d), at one or more later time points during the performance of the physical activity and/or after performing a physical activity, the amount of each of two peptides, GGHPPPP (SEQ ID NO:1) and ESPSLIA (SEQ ID NO:2), in one or more later samples from the subject; f) calculating the ratio of the amount of each of the two peptides of (e) for each later time point to identify one or more later biomarker indices for the subject for each later time point during performance of the physical activity and/or after performing a physical activity, whereby an increase or a lesser decrease in the one or more later biomarker indices of (f) relative to the biomarker indices of (d) over time during the performance of the physical activity and/or after performing the physical activity identifies a decreased level of fatigue in the subject due to physical activity of the subject over time.

The present invention also provides a method of identifying an improvement in physical performance capability of a subject over time, comprising: a) measuring, at a first time point prior to performing a physical activity, the amount of each of two peptides, GGHPPPP (SEQ ID NO:1) and ESPSLIA (SEQ ID NO:2), in a first sample from the subject; b) calculating the ratio of the amount of each of the two peptides of (a) to identify a biomarker index for the subject in the absence of fatigue due to physical activity; c) measuring, at one or more subsequent time points during the performance of the physical activity and/or after performing the physical activity, the amount of each of two peptides, GGHPPPP (SEQ ID NO:1) and ESPSLIA (SEQ ID NO:2), in one or more subsequent samples from the subject; d) calculating the ratio of the amount of each of the two peptides of (c) for each subsequent time point to identify one or more biomarker indices for the subject for each subsequent time point during performance of the physical activity and/or after performing the physical activity, whereby a decrease in the one or more biomarker indices of (d) relative to the biomarker index of (b) over time during the performance of the physical activity and/or after performing the physical activity identifies fatigue in the subject due to physical activity of the subject over time; e) subsequently measuring, after step (d), at one or more later time points during the performance of the physical activity and/or after performing the physical activity, the amount of each of two peptides, GGHPPPP (SEQ ID NO:1) and ESPSLIA (SEQ ID NO:2), in one or more later samples from the subject; f) calculating the ratio of the amount of each of the two peptides of (e) for each later time point to identify one or more later biomarker indices for the subject for each later time point during performance of the physical activity and/or after performing a physical activity, whereby an increase or a lesser decrease in the one or more later biomarker indices of (f) relative to the biomarker indices of (d) over time during the performance of the physical activity and/or after performing the physical activity identifies an improvement in physical performance capability over time.

In the methods of this invention that recite a first time point and one or more subsequent time points or later time points, in some embodiments, the first time point can be prior to performance of a physical activity and the one or more subsequent time points can be during and/or after performance of the physical activity. In some embodiments, the first time point can be during and/or after the performance of physical activity and the one or more later time points can be at a later time following completion of the physical activity.

In the methods of this invention that recite physical activity and/or athletic activity, such physical activity and/or athletic activity can be but is not limited to ultra-endurance exercise, a military operation, military training, running, walking, bicycling, weight lifting, swimming, a standardized physical test course including, for example, those used by the military, a triathlon, a biathlon, shooting of a rifle, shooting of a handgun, the aiming of computerized target equipment, staying awake, hiking, hiking while carrying a large burden on the back, physical activities of daily living and any combination thereof.

As used herein, the term "ultra-endurance exercise" means a single continuous session of physical activity and/or athletic activity during which the subject performs said activity for a minimum of four hours with an average exertion equal to or greater than 70% of ventalitory threshold, as described in Harger-Domitrovich et al., 2007, Medicine & Science in Sports & Exercise. For example, ten hours of continuous repetition of a one-hour exercise regimen consisting of 9 min. of upper-body ergometry, 19 min. of cycling, and 20 min. of treadmill walking with 1-min transition between modes, followed by a 10-min. rest and feeding period.

Military training is defined as the process of preparing military individuals and units to perform their assigned functions and missions, particularly to prepare for combat and wartime functions. "Covering every aspect of military activity, training is the principal occupation of military forces when not actually engaged in combat." (*Brassey's Encyclopedia of Land Forces and Warfare*, By Franklin D. Margiotta). Training may include for example physical tasks such as swimming, hiking when equipped with full military gear, running, moving stealthily, climbing, performing the aforementioned tasks under extreme environmental conditions such as high and low temperatures, high altitude or under conditions where flora and fauna pose significant hazard.

Military operations are defined for the purposes of this instant invention as the activities engaged in by soldiers, sailors and airmen during performance of duties during periods of war and peace. Military operations may include tasks related to engagement of enemy combatants. These tasks may include, but are not limited to the following examples, pursuing the enemy on foot, flying unmanned drone aircraft, operating electronic equipment, manning guns in flight on an airplane, performing law enforcement duties and providing intelligence.

Normal activities of daily living, as defined by the National Cancer Institute, include eating, dressing, getting into or out of a bed or chair, taking a bath or shower, and using the toilet. Instrumental activities of daily living are activities related to independent living and include preparing meals, managing money, shopping, doing housework, and using a telephone.

As used herein, "biomarker" can mean any chemical or biological entity that is produced by cells and/or by commensal flora, or substances that are produced by cells or commensal flora that might be then chemically modified by extracellular enzymes, free radicals produced by cells of the body and/or other naturally occurring processes and that is found, for example, in the saliva, urine, blood, vaginal secretion, tears, feces, sputum, hair, nails, skin, wound fluid, nasal swab, lymph, perspiration, oral mucosa, vaginal mucosa, or the anus, or in serum or plasma obtained from blood. Thus, in the methods of this invention, the sample can be any biological fluid or tissue that can be used in an assay of this invention, including but not limited to, serum, plasma, blood, saliva, semen, lymph, cerebrospinal fluid, prostatic fluid, urine, sputum, joint fluid, body cavity fluid, tear fluid, anal secretions; vaginal secretions, perspiration, whole cells, cell extracts, tissue, biopsy material, aspirates, exudates, slide preparations, fixed cells, tissue sections, etc.

In some embodiments, a biomarker of this invention can be, but is not limited to, a peptide or polypeptide comprising, consisting essentially of and/or consisting of the amino acid sequence GGHPPPP (SEQ ID NO:1) (mw=657.3) and/or ESPSLIA (SEQ ID NO:2) (mw=715.4). Thus, in certain embodiments, the present invention is directed to a peptide or polypeptide as described herein and the present invention can employ or involve one or more of the peptides and polypeptides set forth herein in any method and/or kit of this invention, singly and/or in any combination. In certain other embodiments, the present invention provides a nucleic acid encoding a biomarker of this invention and the methods of this invention can employ or involve.

A biomarker of this invention can be detected and/or quantified in a sample by a variety of methods well known in the art for detecting and/or quantifying substances in biological samples. For example, for detecting and/or quantifying a biomarker that is a peptide or polypeptide, standard methods for detecting and/or quantifying peptides and/or polypeptides in sample can be employed. Nonlimiting examples of such methods include direct protein measurement, immunoassay or other specific binding assay employing an antibody or ligand that specifically binds a peptide or polypeptide, protein separation assays such as electrophoresis, gas chromatography (GC), high performance liquid chromatography (HPLC), mass spectrometry (MS), etc., as are well known in the art. Other methods of detection may include bioassays using mammalian or bacterial cells wherein an output is proportional to the concentration of peptide in the sample solution, solid phase methods wherein binding to a surface coated with a peptide recognizing molecule triggers an output electrical signal or change in optical property.

For detection and/or quantification of a nucleic acid encoding a biomarker of this invention, standard methods for detection and/or quantification of nucleic acids in a sample can be employed. Non-limiting examples include hybridization assays, amplification assays, sequencing protocols, etc., as are well known in the art.

The term "biomarker index" or "fatigue biomarker index" (FBI) means the ratio of the peak height or peak area of the ion intensity for GGHPPPP (SEQ ID NO:1) to the ion intensity of ESPSLIA when said ions are detected in a mass spectrometer, e.g., ion-trap mass spectrometer; in addition, the biomarker index may be any other ratiometric measure derived from the ratio of the concentration of GGHPPPP (SEQ ID NO:1) to the concentration of ESPSLIA, such as a ratio of fluorescence intensities in an immunoassay, a ratio of counts in a radioactivity-based assay and/or a ratio of optical densities in an enzyme-linked immunoassay.

In some embodiments of this invention, the biomarker index is calculated by determining the ratio of the peak heights of each of the two peptides, GGHPPPP (SEQ ID NO:1) and ESPSLIA, where said peaks are produced using liquid chromatography with an ion-trap mass spectrometer. In some embodiments of this invention, the biomarker index is calculated by determining the ratio of the peak areas of each of the two peptides, GGHPPPP (SEQ ID NO:1) and ESPSLIA, where said peaks are produced using liquid chromatography with an ion-trap mass spectrometer.

In the methods of this invention employing measurements over time, the time intervals can be minutes, hours, days, weeks, months and/or years in any order and in any combination.

A subject of this invention is any animal in which identification of fatigue, recovery from fatigue and/or physical performance capability is needed or desired. In some embodiments, the subject is mammal and in most embodiments is a human. In other embodiments, the subject can be a horse, a dog or any other mammal about which the information obtained from the methods of this invention is needed or desired.

The terms "fatigue" and "fatigued state" as used herein mean weariness or exhaustion from labor, exertion, exercise, or stress, including loss of physical strength and bodily and mental capabilities.

Also as used herein, the term "rested" or "rested state" or "non-fatigued state" means having sufficient rest from bodily and/or mental exertion, either before physical exercise and/or after recovery from fatigue.

"Perceived level of fatigue" as used herein means an individual's personal estimate or assessment of their fatigue and their ability to carry out tasks requiring a certain level of physical and/or cognitive performance.

In addition, as used herein, "physical performance capability" means the capacity to accomplish a task which requires expenditure of a particular amount of energy. These tasks include, but are not limited to lifting objects, carrying objects, maintaining a certain pace of walking, running and/or cycling and maintaining a particular heart rate for a specified period. Capability represents a subject's potential for energy expenditure over a particular period of time.

The term "fitness" as used herein means good health or physical condition, especially as the result of exercise and proper nutrition.

In some embodiments, a population of study subjects of this invention includes healthy male and/or female volunteers less than the age of 42 that are in good physical condition and not suffering from known diseases and/or healthy young (less than 25 years old) military members being screened for selection to Special Forces in the United States Military.

To perform a physical activity and/or athletic activity at a sufficient level means the ability to perform a task at a level that is required for professional advancement, required to pass a test, and/or required to complete a study. This also may include but is not limited to meeting individual personal physical and performance goals, satisfying job eligibility requirements, and/or meeting criteria required to continue working at a task, for example determining whether a person is too fatigued to drive a truck.

The present invention further contemplates methods of this invention wherein a subject identified as being fatigued, being in a fatigued state, having an increased level of fatigue, having a decrease in physical performance capability and/or having a decreased likelihood of performing a physical activity at a sufficient level can be exposed to or contacted with a performance enhancing material and/or activity, after which the subject can be evaluated for recovery from fatigue, recovery from a fatigued state, a decrease in the level of fatigue in the subject, improvement or increase in physical performance capability and/or an increased likelihood of performing a physical activity at a sufficient level by employing the methods of this invention during and/or after the subject is exposed to and/or contacted with the performance enhancing material and/or undergoes a performance enhancing activity.

As one example of a method that employs performance-enhancing material and/or activity, the present invention provides a method of identifying an improvement in physical performance capability of a subject upon exposure to and/or contact with a performance-enhancing material and/or activity, comprising:

a) measuring, at a first time point prior to performing a physical activity and in the absence of contact with or exposure to the performance enhancing material, the amount of each of two peptides, GGHPPPP (SEQ ID NO:1) and ESPSLIA (SEQ ID NO:2), in a first sample from the subject;

b) calculating the ratio of the amount of each of the two peptides of (a) to identify a biomarker index for the subject in the absence of fatigue due to physical activity;

c) measuring, at one or more subsequent time points during the performance of the physical activity and/or after performing the physical activity, the amount of each of two peptides, GGHPPPP (SEQ ID NO:1) and ESPSLIA (SEQ ID NO:2), in one or more subsequent samples from the subject;

d) calculating the ratio of the amount of each of the two peptides of (c) for each subsequent time point to identify one or more biomarker indices for the subject for each subsequent time point during performance of the physical activity and/or after performing the physical activity, whereby a decrease in the one or more biomarker indices of (d) relative to the biomarker index of (b) identifies fatigue in the subject due to physical activity of the subject;

e) contacting and/or exposing the subject to a performance-enhancing material and/or activity and repeating steps (a)-(d) above as steps (a')-(d'), whereby an increase or a lesser decrease in the biomarker index of (d') relative to the biomarker index of (b') identifies an improvement in physical performance capability in the subject upon exposure to or contact with the performance enhancing material and/or activity. It would be well understood by one of ordinary skill in the art that any of the methods of this invention (e.g., involving fatigue, recovery from fatigue, likelihood of performing a physical activity at a sufficient level, etc.) can be modified as described in the example above to incorporate the use of performance enhancing material and/or activity.

In the methods of the present invention, the performance enhancing material can be, but is not limited to, a dietary or nutritional supplement or food that comprises or consists primarily of sugars and carbohydrates; a nutritional supplement that contains fenugreek or fenugreek extracts; a nutritional supplement that is composed in part of antioxidants including vitamins C and E; green tea extract; an extract of the Aloe vera plant; melatonin; essential, non-essential and chemically modified amino acids; selenium; cobalt; magnesium; 1-alpha-carnitine; amphetamine; modafinil; creatinine; a dietary supplement composed principally of proteins including whey protein and yeast protein; anabolic steroids; and/or erythropoietin, ephedrine; ginseng; caffeine; forskolin; glutamine, arginine, whey protein; soy protein; egg albumin; casein; (nutritional compound described in U.S. Pat. No. 6,051,236 as a dry powder comprising protein, amino acids, CHO, vitamins C and E); growth hormone; vitamins, minerals; essential fatty acids; tricarboxylic acid cycle intermediates; free fatty acids; pyruvate; creatine; ipriflavone; pentose (e.g., a monosaccharide such as ribose, D-ribose, ribulose, xylitol, xylulose, any five carbon precursor of ribose; cortisol blockers (e.g., phosphatidylserine, HMB, DHEA, CLA, anabolic steroids, creatine monohydrates, pregnenalone, Ipriflavone, super physiological levels of leucine, anabolic steroids, antioxidants, leucine metabolites, glutamic acid and its metabolites, glutamine and androstenedione).

Furthermore, in the methods of this invention, the performance enhancing activity can be but is not limited to an exercise regimen that incorporates strength training and/or aerobic exercise; massage therapy; meditation; biofeedback; hypnosis; blood doping; isometrics, yoga, acupuncture; aromatherapy; device that emits electromagnetic energy including light and magnetism; and/or counseling.

In addition, in the methods of this invention, the performance enhancing material can be but is not limited to a device that emits photons in the near infra-red spectrum to increase energy output in muscles; clothing, including pants, shorts, socks, briefs, underwear, footwear, orthotics, ankle, knee and leg supports, orthotics and/or other devices designed to increase physical performance and/or reduce fatigue; clothing, wraps, supports and/or other devices that cool muscles; strength training machines/apparatus; endurance machines/apparatus; and/or exercise equipment.

In some embodiments of this invention, the method can include the measurement of an internal standard from the subject, which can be, for example, an endogenously produced protein, glycoprotein and/or polymer, to normalize the concentration[s] of biomarker[s] measured. This can be done, for example, to correct for relative dilution or other alteration of the body fluids and/or tissues of the subject that are used as the sample in the methods described herein. For example, if there is a 10% change in the internal standard upon carrying out the methods of this invention, then it may be necessary to adjust the values obtained in measurement of the biomarker by 10% to normalize these values. Such changes to the internal standard and the test sample can be due to various physiological conditions that can be present or absent in the subject, including, but not limited to, the level of hydration of the subject, the presence or absence of drugs or other substances in the subject that can exert a physiological effect on the subject, the overall level of fitness of the subject, drugs that reduce the volume of saliva produced, including e.g., anticholinergics, and others, drugs that increase the volume of saliva, surgery, radiation, exposure to chemotherapy that may reduce the volume of saliva, and/or other substances, congenital abnormalities that lead to increased or reduced secretion of proteins and/or other substances and/or that lead to a change in biomarker content or water in saliva, and/or bacteria that may produce large amounts of substances, including proteins, that are not associated with those secreted by the body. A nonlimiting list of internal standards of this invention includes alpha-amylase, total protein per unit volume of saliva, sodium, calcium, chloride ion, and/or IgA.

The biomarkers and biomarker indices of this invention are correlated with fatigue, a fatigued state, an increase or decrease in fatigue, an increase or decrease in physical performance, a subject's perceived level of fatigue, recovery from a fatigued state, and/or an increased or decreased likelihood of performing a physical activity at a sufficient level as described herein according to methods well known in the art and as disclosed in the Examples provided herein. In general, identifying such correlation involves conducting analyses that establish a statistically significant association and/or a statistically significant correlation between the presence of a biomarker or biomarker index or a combination of biomarkers or biomarker indices and a change in the subject (e.g., from rested to fatigued state, during and/or after performance of physical activity or other defined or standardized activity) as detected according to standard methods. An analysis that identifies a statistical association (e.g., a significant association) between the biomarker or biomarker index or between the combination of biomarkers or biomarker indices and the change in the subject establishes a correlation between the increase or decrease of the biomarker or biomarker index or combination of biomarkers or biomarker indices in a subject and the change being analyzed.

It would be well understood by one of skill in the art that the methods of the present invention can be carried out on multiple subjects and the data compiled to produce mean and median values that indicate fatigue, a fatigued state, an increase or decrease in fatigue, an increase or decrease in physical performance, a subject's perceived level of fatigue, recovery from a fatigued state, and/or an increased or decreased likelihood of performing a physical activity at a sufficient level according to this invention. It would also be understood that the statistical limits described by the data obtained from groups of subjects can be applied to individual subjects' response. Thus, it would be understood that in some embodiments of this invention, the methods of this invention can be carried out using a computer database, wherein the data from multiple subjects are stored in a computer database and analyzed according to art-known methods of statistical and mathematical analysis to identify means, medians, trends, statistically significant changes, variances, etc.

Thus, in some embodiments, the methods of this invention can be carried out using a computer database. Thus the present invention provides a computer-assisted method of identifying fatigue, a fatigued state, an increase or decrease in fatigue, an increase or decrease in physical performance, a subject's perceived level of fatigue, recovery from a fatigued state, and/or an increased or decreased likelihood of performing a physical activity at a sufficient level. The method involves the steps of (a) storing a database of biological data for a plurality of subjects, the biological data that is being stored including for each of said plurality of subjects: (i) a description of the status of the subject and/or physical/athletic activity performed by the subject, (ii) a description of any performance enhancing material and/or activity administered to, contacted with and/or implemented by the subject; (iii) a description of measurements according to art-known methods detecting a change in the status or performance in the subject; and (iv) a description of measurements of biomarkers or biomarker indices in the subject; and then (b) querying the database to determine the relationship between a change in the measurement of biomarkers or biomarker indices in the subject and change in performance or status of the subject. Such querying can be carried out prospectively or retrospectively on the database by any suitable means, but is generally done by statistical analysis in accordance with known techniques, as described herein.

Compositions of the Invention

Further aspects of the present invention include an isolated peptide comprising the amino acid sequence GGHPPPP (SEQ ID NO:1), an isolated peptide comprising the amino acid sequence ESPSLIA (SEQ ID NO:2) and a composition comprising either or both of these isolated peptides in a pharmaceutically acceptable carrier.

Thus, in particular embodiments, the present invention provides a biomarker protein or peptide of this invention, a nucleic acid comprising a nucleotide sequence encoding a biomarker protein or peptide of this invention, a vector comprising said nucleic acid and a cell containing said vector. The biomarker, the nucleic acid, the vector and/or the cell can be present singly and/or in any combination in a composition comprising a pharmaceutically acceptable carrier.

In other embodiments of this invention, a nucleic acid having the nucleotide sequence or a substantially similar nucleotide sequence of the gene encoding a biomarker protein or peptide of this invention can be used as a probe in a nucleic acid hybridization assay for the detection of nucleic acid encoding a biomarker protein or peptide in various tissues and/or body fluids of a subject of this invention. The probe can be used in any type of nucleic acid hybridization assay including Southern blots (Southern, 1975, *J. Mol. Biol.* 98:508), Northern blots (Thomas et al., 1980, *Proc. Natl Acad. Sci.* U.S.A. 77:5201-05), colony blots (Grunstein et al., 1975, *Proc. Natl Acad. Sci.* U.S.A. 72:3961-65), slot blots, dot blots, etc. Stringency of hybridization can be varied depending on the requirements of the assay according to methods well known in the art. Assays for detecting nucleic acid encoding a protein in a cell, or the amount thereof, typically involve first contacting the cells or extracts of the cells containing nucleic acids therefrom with an oligonucleotide probe that specifically binds to nucleic acid encoding a protein or peptide as described herein (typically under conditions that permit access of the oligonucleotide to intracellular material), and then detecting the presence or absence of binding of the oligonucleotide probe thereto. Any suitable assay format can be employed (see, e.g., U.S. Pat. No. 4,358, 535; U.S. Pat. Nos. 4,302,204; 4,994,373; 4,486,539; 4,563, 419; and 4,868,104, the disclosures of each of which are incorporated herein by reference in their entireties).

As used herein, the terms peptide and polypeptide are used to describe a chain of amino acids, which correspond to those encoded by a nucleic acid. A peptide usually describes a chain of amino acids of from two to about 30 amino acids and polypeptide usually describes a chain of amino acids having more than about 30 amino acids. The term polypeptide can refer to a linear chain of amino acids or it can refer to a chain of amino acids, which have been processed and folded into a functional protein. It is understood, however, that 30 is an arbitrary number with regard to distinguishing peptides and polypeptides and the terms may be used interchangeably for a chain of amino acids around 30. The peptides and polypeptides of the present invention can be obtained by isolation and purification of the peptides and polypeptides from cells or body fluids or tissues where they are found naturally or by expression of a recombinant and/or synthetic nucleic acid encoding the peptide or polypeptide. The peptides and polypeptides of this invention can be obtained by chemical synthesis, by proteolytic cleavage of a polypeptide and/or by synthesis from nucleic acid encoding the peptide or polypeptide.

It is also understood that the peptides and polypeptides of this invention may also contain conservative substitutions where a naturally occurring amino acid is replaced by one having similar properties and which does not alter the function of the peptide or polypeptide. Such conservative substitutions are well known in the art. Thus, it is understood that, where desired, modifications and changes can be made in the nucleic acid sequence of the underlying gene(s) and/or amino acid sequence of the peptides and polypeptides of the present invention and still obtain a peptide or polypeptide having like or otherwise desirable characteristics. Such changes can occur in natural isolates or can be synthetically introduced using site-specific mutagenesis, the procedures for which, such as mismatch polymerase chain reaction (PCR), are well known in the art. One of skill in the art will also understand that polypeptides and nucleic acids that contain modified amino acids and nucleotides, respectively (e.g., to increase the half-life and/or the therapeutic efficacy of the molecule), can be used in the methods of the invention.

"Nucleic acid" as used herein refers to single- or double-stranded molecules which may be DNA, comprised of the nucleotide bases A, T, C and G, or RNA, comprised of the bases A, U (substitutes for T), C, and G. The nucleic acid may represent a coding strand or its complement. Nucleic acids may be identical in sequence to a sequence that is naturally occurring or may include alternative codons that encode the same amino acid as that which is found in the naturally occurring sequence. Furthermore, nucleic acids may include codons that represent conservative substitutions of amino acids as are well known in the art. The nucleic acids of this invention can also comprise any nucleotide analogs and/or derivatives as are well known in the art.

As used herein, the term "isolated nucleic acid" means a nucleic acid separated or substantially free from at least some of the other components of the naturally occurring organism, for example, the cell structural components commonly found associated with nucleic acids in a cellular environment and/or other nucleic acids. The isolation of nucleic acids can therefore be accomplished by well-known techniques such as cell lysis followed by phenol plus chloroform extraction, followed by ethanol precipitation of the nucleic acids. The nucleic acids of this invention can be isolated from cells according to methods well known in the art for isolating nucleic acids. Alternatively, the nucleic acids of the present invention can be synthesized according to standard protocols well described in the literature for synthesizing nucleic acids. Modifications to the nucleic acids of the invention are also contemplated, provided that the essential structure and function of the peptide or polypeptide encoded by the nucleic acid are maintained.

The present invention further provides a kit for detection and/or quantification of the biomarkers of this invention. In some embodiments, such a kit can comprise one or more antibodies, ligands and/or aptamers, along with suitable buffers, wash solutions, dilution buffers, secondary antibodies, detection reagents, etc., for the detection of antigen/antibody complex formation, ligand/target complex formation and/or aptamer/target complex formation under various conditions. In another embodiment, a kit of this invention can comprise a nucleic acid probe or primer that is complementary to a nucleotide sequence encoding a biomarker of this invention, along with suitable buffers, wash solutions, dilution buffers, detection reagents, etc. for the amplification of target nucleic acid and/or detection of nucleic acid hybridization under various conditions.

Thus, in some embodiments, the present invention provides a kit comprising an antibody that specifically reacts with a biomarker of this invention and reagents for detecting antigen/antibody complex formation.

Further provided is a kit comprising an aptamer that specifically reacts with a biomarker of this invention and reagents for detecting aptamer/target molecule complex formation.

In addition, a kit is provided herein, comprising a nucleic acid that hybridizes under high stringency conditions with a nucleic acid encoding a biomarker of this invention and reagents for detecting nucleic acid hybridization complex formation.

Screening Methods

In addition, the present invention provides a method of identifying a substance that binds a peptide of this invention, comprising contacting the peptide with a test compound under conditions whereby binding between the peptide and the test compound can be detected; and detecting binding between the polypeptide and the test compound.

Further provided is a method of identifying a substance having the ability to inhibit or enhance the binding activity of a peptide of this invention, comprising contacting the substance with the peptide under conditions whereby binding can occur and detecting a decrease or increase in the amount of binding in the presence of the substance as compared to a control amount of binding in the absence of the substance, thereby identifying a substance having the ability to inhibit or enhance the binding activity of the peptide.

For the methods of this invention that employ the detection of binding, such assays are well known in the art and can employ, for example, an antibody, ligand and/or aptamer that binds a peptide of this invention either directly or indirectly.

Also provided herein is a method of identifying a compound that modulates the activity of a peptide of this invention, comprising contacting the peptide with a test compound under conditions whereby modulation of the activity of the peptide can be detected. Because there is an association between fatigue and reduction in levels of GGHPPPP SEQ ID NO:1) and increase in ESPSLIA (SEQ ID NO:2), the peptides may serve a role in, for example, communicating a state of high energy demand to target organs, altering function of organs involved in mobilization of energy, modulating the activity of organs involved with the mobilization of energy stores including adipose tissue, the liver and muscle, modulating the activity of gastrointestinal mucosal leading to increased absorption of sugars, converting amino acids to sugars, or modifying the metabolic and enzymatic activity of commensal bacteria residing in the gastrointestinal tract leading to increased availability of sugars and free fatty acids that can be used to accomplish physical work by voluntary muscle, modulating the activity of the liver, pancreas, duodenum and other organs that secrete enzymes, emulsifiers and other substances that affect the processing of food, altering the distribution and targeting of sugars, lipids and proteins in the blood. These activities can be measured using in vitro cell-based assays with various output functions that can be used to determine activity, cell-free assays that measure association with specific receptors or important regulatory molecules, gene expression assays, and methods that involve measurement of functional outputs or alterations of metabolic production, fat mobilization and other phenomenon associated with fatigue or the ability to perform physical and cognitive tasks.

Additionally, the present invention provides a method of identifying immunomodulating activity in a peptide of this invention, specifically by employing the peptide in an assay for immunomodulating activity and detecting immunomodulating activity in the presence of the peptide as compared to a control, thereby identifying immunomodulating activity in the peptide. In this method, the assay for immunomodulating activity can be, but is not limited to, antibody production (or other assay to detect humoral immune response, T cell activation (or other assay to detect cellular immune response), nitric oxide production, interleukin 2 (IL-2) secretion and any combination thereof.

Furthermore, a method is provided herein of identifying antimicrobial and/or antifungal activity in a peptide of this invention, comprising employing the peptide in an assay for antimicrobial and/or antifungal activity and detecting antimicrobial and/or antifungal activity in the presence of the peptide as compared to a control, thereby identifying antimicrobial and/or antifungal activity in the peptide. Protocols for identifying antimicrobial and/or antifungal activity in a substance are well known in the art.

The term "antibody" as used herein, includes, but is not limited to a polypeptide encoded by an immunoglobulin gene or immunoglobulin genes, or a fragment thereof. "Antibody" also includes, but is not limited to, a polypeptide encoded by an immunoglobulin gene or immunoglobulin genes, or a fragment thereof, which specifically binds to and recognizes the biomarkers of this invention.

The term "epitope" means an antigenic determinant that is specifically bound by an antibody. Epitopes usually consist of surface groupings of molecules such as amino acids and/or sugar side chains and usually have specific three-dimensional structural characteristics, as well as specific charge characteristics.

The terms "specifically binds to" and "specifically reactive with" refer to a binding reaction that is determinative of the presence of the antigen and antibody or aptamer and target in the presence of a heterogeneous population of proteins, nucleic acids and/or other biologics. Thus, under designated assay conditions, the specified antibodies and antigens and/or aptamers and targets bind to one another and do not bind in a significant amount to other components present in a sample.

In some embodiments employing antibodies, a variety of immunoassay formats can be used to select antibodies specifically reactive with a particular antigen. For example, solid-phase ELISA immunoassays are routinely used to select monoclonal antibodies specifically immunoreactive with an analyte. See Harlow and Lane (ANTIBODIES: A LABORATORY MANUAL, Cold Springs Harbor Publications, New York, (1988)) for a description of immunoassay formats and conditions that can be used to determine specific immunoreactivity. Typically a specific or selective reaction will be at least twice background signal to noise and more typically more than 10 to 100 times greater than background.

An "immunologically reactive fragment" of a protein refers to a portion of the protein or peptide that is immunologically reactive with a binding partner, e.g., an antibody, which is immunologically reactive with the protein itself.

Antibodies to biomarkers of this invention can be generated using methods that are well known in the art. Such antibodies can include, but are not limited to, polyclonal, monoclonal, chimeric, humanized, single chain, Fab fragments, and/or fragments produced by an expression library, including e.g., phage display. (See, e.g., Paul, FUNDAMENTAL IMMUNOLOGY, 3rd Ed., 1993, Raven Press, New York, for antibody structure and terminology.)

Antibody fragments that contain specific binding sites for a biomarker of this invention can also be generated. For example, such fragments include, but are not limited to, the F(ab')$_2$ fragments that can be produced by pepsin digestion of the antibody molecule, and the Fab fragments that can be generated by reducing the disulfide bridges of the F(ab')$_2$ fragments. Alternatively, Fab expression libraries can be constructed to allow rapid and easy identification of monoclonal Fab fragments with the desired specificity (Huse et al., Science 254, 1275-1281 (1989)).

For the production of antibodies, various hosts including goats, rabbits, rats, mice, humans, and others, may be immunized by injection with a protein or any fragment or oligopeptide or conjugate thereof that has immunogenic properties. Depending on the host species, various adjuvants can be used to increase the immunological response. Such adjuvants include, but are not limited to, Freund's complete and incomplete adjuvant, mineral gels such as aluminum hydroxide, and surface active substances such as lysolecithin, pluronic polyols, polyanions, peptides, oil emulsions, keyhole limpet hemocyanin, and dinitrophenol. Examples of adjuvants used in humans include BCG (bacilli Calmette-Guerin) and *Corynebacterium parvum*.

Monoclonal antibodies can be prepared using any technique that provides for the production of antibody molecules by continuous cell lines in culture. These include, but are not limited to, the hybridoma technique, the human B-cell hybridoma technique, and the EBV-hybridoma technique (Kohler et al. (1975) *Nature* 256:495-497; Kozbor et al. (1985) *J. Immunol. Methods* 81:31-42; Cote et al. (1983) *Proc. Natl. Acad. Sci.* 80:2026-2030; Cole et al. (1984) *Mol. Cell Biol.* 62:109-120). Briefly, the procedure can be as follows: an animal is immunized with a protein or immunogenic fragment or oligopeptide or conjugate thereof. Lymphoid cells (e.g., splenic lymphocytes) are then obtained from the immunized animal and fused with immortalizing cells (e.g., myeloma or heteromyeloma) to produce hybrid cells. The hybrid cells are screened to identify those that produce the desired antibody.

Human hybridomas that secrete human antibody can be produced by the Kohler and Milstein technique and according to art-known protocols. Hybridoma production in rodents, especially mouse, is a very well established procedure and thus, stable murine hybridomas provide an unlimited source of antibody of select characteristics. As an alternative to human antibodies, the mouse antibodies can be converted to chimeric murine/human antibodies by genetic engineering techniques. See Oi et al., *Bio Techniques* 4(4):214-221 (1986); Sun et al., *Hybridoma* 5 (1986).

The monoclonal antibodies of this invention specific for biomarker protein epitopes of this invention can also be used to produce anti-idiotypic (paratope-specific) antibodies. (See e.g., McNamara et al., *Science* 220, 1325-26 (1984); Kennedy et al., *Science* 232:220 (1986).) These antibodies resemble the biomarker protein epitope and thus can be used as an antigen to stimulate an immune response against the biomarker protein.

In addition, techniques developed for the production of "chimeric antibodies," the splicing of mouse antibody genes to human antibody genes to obtain a molecule with appropriate antigen specificity and biological activity can be used (Morrison et al. *Proc. Natl. Acad. Sci.* 81:6851-6855 (1984); Neuberger et al., *Nature* 312:604-608 (1984); Takeda et al., *Nature* 314:452-454 (1985)). Alternatively, techniques described for the production of single chain antibodies can be adapted, using methods known in the art, to produce biomarker protein-specific single chain antibodies. Antibodies with related specificity, but of distinct idiotypic composition, can be generated by chain shuffling from random combinatorial immunoglobin libraries (Burton, *Proc. Natl. Acad. Sci.* 88:11120-3 (1991)).

Antibodies can also be produced by inducing in vivo production in the lymphocyte population or by screening immunoglobulin libraries or panels of highly specific binding reagents as described in the literature (Orlandi et al., *Proc. Natl. Acad. Sci.* 86:3833-3837 (1989)); Winter et al., *Nature* 349:293-299 (1991)).

Various immunoassays can be used to identify biomarkers of this invention. Such immunoassays typically involve the measurement of antigen/antibody complex formation between a biomarker protein or peptide and its specific antibody.

The immunoassays of the invention can be either competitive or noncompetitive and both types of assays are well-known and well-developed in the art. In competitive binding assays, antigen or antibody competes with a detectably labeled antigen or antibody for specific binding to a capture site bound to a solid surface. The concentration of labeled antigen or antibody bound to the capture agent is inversely proportional to the amount of free antigen or antibody present in the sample.

Noncompetitive assays of this invention can be sandwich assays, in which, for example, the antigen is bound between two antibodies. One of the antibodies is used as a capture agent and is bound to a solid surface. The other antibody is labeled and is used to measure or detect the resultant antigen/antibody complex by e.g., visual or instrument means. A number of combinations of antibody and labeled antibody can be used, as are well known in the art. In some embodiments, the antigen/antibody complex can be detected by other proteins capable of specifically binding human immunoglobulin constant regions, such as protein A, protein L or protein G. These proteins are normal constituents of the cell walls of streptococcal bacteria. They exhibit a strong nonimmunogenic reactivity with immunoglobulin constant regions from a variety of species. (See, e.g., Kronval et al., *J. Immunol.*, 111:1401-1406 (1973); Akerstrom et al., *J. Immunol.*, 135: 2589-2542 (1985).)

In some embodiments, the non-competitive assays need not be sandwich assays. For instance, the antibodies or antigens in the sample can be bound directly to the solid surface. The presence of antibodies or antigens in the sample can then be detected using labeled antigen or antibody, respectively.

In some embodiments, antibodies and/or proteins can be conjugated or otherwise linked or connected (e.g., covalently or noncovalently) to a solid support (e.g., bead, plate, slide, dish, membrane or well) in accordance with known techniques. Antibodies can also be conjugated or otherwise linked or connected to detectable groups such as radiolabels (e.g., $^{35}S$, $^{125}I$, $^{32}P$, $^{3}H$, $^{14}C$, $^{131}I$), enzyme labels (e.g., horseradish peroxidase, alkaline phosphatase), gold beads, chemiluminescence labels, ligands (e.g., biotin) and/or fluorescence labels (e.g., fluorescein) in accordance with known techniques.

A variety of organic and inorganic polymers, both natural and synthetic can be used as the material for the solid surface. Nonlimiting examples of polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials that can be used include, but are not limited to, include paper, glass, ceramic, metal, metalloids, semiconductive materials, cements and the like. In addition, substances that form gels, such as proteins (e.g., gelatins), lipopolysaccharides, silicates, agarose and polyacrylamides can be used. Polymers that form several aqueous phases, such as dextrans, polyalkylene glycols or surfactants, such as phospholipids, long chain (12-24 carbon atoms) alkyl ammonium salts and the like are also suitable. Where the solid surface is porous, various pore sizes can be employed depending upon the nature of the system.

A variety of immunoassay systems can be used, including but not limited to, radio-immunoassays (RIA), enzyme-linked immunosorbent assays (ELISA) assays, enzyme immunoassays (EIA), "sandwich" assays, gel diffusion precipitation reactions, immunodiffusion assays, agglutination assays, immunofluorescence assays, fluorescence activated cell sorting (FACS) assays, immunohistochemical assays, protein A immunoassays, protein G immunoassays, protein L immunoassays, biotin/avidin assays, biotin/streptavidin assays, immunoelectrophoresis assays, precipitation/flocculation reactions, immunoblots (Western blot; dot/slot blot); immunodiffusion assays; liposome immunoassay, chemiluminescence assays, library screens, expression arrays, etc., immunoprecipitation, competitive binding assays and immunohistochemical staining. These and other assays are described, among other places, in Hampton et al. (*Serological Methods, a Laboratory Manual*, APS Press, St Paul, Minn. (1990)) and Maddox et al. (*J. Exp. Med.* 158:1211-1216 (1993); the entire contents of which are incorporated herein by reference for teachings directed to immunoassays).

The methods of this invention can also be carried out using a variety of solid phase systems, such as described in U.S. Pat. No. 5,879,881, as well as in a dry strip lateral flow system (e.g., a "dipstick" system), such as described, for example, in U.S. Patent Publication No. 20030073147, the entire contents of each of which are incorporated by reference herein.

In some embodiments, the biomarker of this invention can be detected and/or quantified in an assay employing an aptamer, a molecule that binds tightly to the biomarker in a manner similar to an antibody, a ligand or a small molecule. As used herein, the term "aptamer" includes any nucleic acid molecule or small peptide that specifically recognizes and binds a target molecule (e.g., a target peptide such as a biomolecule of this invention). An "oligonucleotide-based aptamer" is defined as an aptamer made primarily, although not exclusively, from DNA and/or RNA bases. A "peptide-based aptamer" is defined as an aptamer made primarily, although not exclusively, from amino acids.

In some embodiments, an aptamer can be a small, usually stabilized, nucleic acid molecule that includes a binding domain for a target molecule (e.g., a biomarker of this invention). Oligonucleotide-based aptamers of this invention are oligonucleotides, or short (typically <100 bp) polymers of either DNA or RNA, that have been selected from random pools based on their ability to bind nucleic acid, proteins, small organic compounds, and even entire organisms, usually with high affinity.

Oligonucleotide-based aptamers are typically developed to bind particular ligands using a previously described selection technique referred to as SELEX (Systematic Evolution of Ligands by Exponential Enrichment). This technique allows for selection of aptamers both in vivo and in vitro. Methods of making aptamers are described in several publications, for example, Ellington and Szostak, *Nature* 346:818 (1990), Tuerk and Gold, *Science* 249:505 (1990), U.S. Pat. No. 5,582,981, PCT Publication No. WO 00/20040, U.S. Pat. No. 5,270,163, Lorsch and Szostak, *Biochemistry*, 33:973 (1994), Mannironi et al., *Biochemistry* 36:9726 (1997), Blind, *Proc. Nat'l. Acad. Sci. USA* 96:3606-3610 (1999), Huizenga and Szostak, *Biochemistry*, 34:656-665 (1995), PCT Publication Nos. WO 99/54506, WO 99/27133, WO 97/42317 and U.S. Pat. No. 5,756,291.

Generally, in their most basic form, in vitro selection techniques for identifying oligonucleotide-based aptamers involve first preparing a large pool of oligonucleotides of the desired length that contain at least some central region that is randomized or mutagenized. For instance, a common oligonucleotide pool for aptamer selection might contain a region of 20-100 randomized nucleotides flanked on both ends by a relatively short (15-25 bp) region of nucleotides with defined sequence useful for the binding of PCR primers. The oligonucleotide pool is amplified using standard PCR techniques.

The original oligonucleotide pool is typically made of DNA bases. However, before the selection step, it can be converted to RNA bases using in vitro transcription methods well known in the art. During the selection step, the oligonucleotide library is allowed to interact with the target molecule, which is either free in solution or adhered to a physical surface such as a bead. In either case, the chemical environment of the interaction is typically controlled to simulate conditions anticipated for the final application of the invention, for example temperature, pH and osmolality matched to physiological conditions. When selection occurs in solution, capillary electrophoresis is used to separate bound from unbound oligonucleotides. For selection methods that use solid surfaces, bound and unbound oligonucleotide are separated by several rounds of washing of the surface. Bound oligonucleotide is isolated and amplified using standard PCR techniques. If the library was converted from DNA to RNA before selection, then reverse transcription must be used prior to PCR amplification. The amplified oligonucleotide sequences are then put through another round of the same type of selection. Typically, the selection process requires a total of three to ten iterative rounds to produce a high-affinity aptamer. In the final step, the amplified DNA is cloned and sequenced using standard procedures to identify the sequence of the oligonucleotides that are capable of acting as aptamers for the target molecule. Once a sequence has been identified for a tightly binding oligonucleotide-based aptamer, the nucleotide-based aptamer may be further refined and optimized for binding affinity by performing additional rounds of selection starting from a pool of oligonucleotides containing controlled levels of randomized mutations of the original oligonucleotide sequence.

In further embodiments, an oligonucleotide-based aptamer can include at least one modified nucleotide base. The term "modified nucleotide base" encompasses nucleotides with a covalently modified base and/or sugar. For example, modified nucleotides include nucleotides having sugars that are covalently attached to low molecular weight organic groups other than a hydroxyl group at the 3' position and other than a phosphate group at the 5' position. Such modified nucleotides can also include 2' substituted sugars such as 2'-O-methyl; 2'-O-alkyl; 2'-O-allyl; 2'-S-alkyl; 2'-S-allyl; 2'-fluoro; 2'-halo; or 2'-azido-ribose, carbocyclic sugar analogues, a-anomeric sugars; epimeric sugars such as arabinose, xyloses or lyxoses, pyranose sugars, furanose sugars, and sedoheptulose.

Modified nucleotides of this invention can include but are not limited to, alkylated purines and/or pyrimidines; acylated purines and/or pyrimidines; and other heterocycles. These classes of pyrimidines and purines are known in the art and include, pseudoisocytosine; N4, N4-ethanocytosine; 8-hydroxy-N6-methyladenine; 4-acetylcytosine, 5-(carboxyhydroxylmethyl)uracil; 5-fluorouracil; 5-bromouracil; 5-carboxymethylaminomethyl-2-thiouracil; 5-carboxymethylaminomethyl uracil; dihydrouracil; inosine; N6-isopentyl-adenine; 1-methyladenine; 1-methylpseudouracil; 1-methylguanine; 2,2-dimethylguanine; 2-methyladenine; 2-methylguanine; 3-methylcytosine; 5-methylcytosine; N6-methyladenine; 7-methylguanine; 5-methylaminomethyl uracil; 5-methoxy amino methyl-2-thiouracil; β-D-mannosylqueosine; 5-methoxycarbonylmethyluracil; 5-methoxyuracil; 2 methylthio-N6-isopentenyladenine; uracil-5-oxyacetic acid methyl ester; psuedouracil; 2-thiocytosine; 5-methyl-2 thiouracil, 2-thiouracil; 4-thiouracil; 5-methyluracil; N-uracil-5-oxyacetic acid methylester; uracil 5-oxyacetic acid; queosine; 2-thiocytosine; 5-propyluracil; 5-propylcytosine; 5-ethyluracil; 5-ethylcytosine; 5-butyluracil; 5-pentyluracil; 5-pentylcytosine; and 2,6,-diaminopurine; methylpsuedouracil; 1-methylguanine; and 1-methylcytosine.

Oligonucleotide-based aptamers of this invention can be synthesized from conventional phosphodiester linked nucleotides using standard solid or solution phase synthesis techniques that are known in the art. Linkages between nucleotides can use alternative linking molecules. For example, linking groups of the formula P(O)S, (thioate); P(S)S, (dithioate); P(O)NR'2; P(O)R'; P(O)OR6; CO; or CONR'2 wherein R is H (or a salt) or alkyl (1-12C) and R6 is alkyl (1-9C) is joined to adjacent nucleotides through —O— or —S—.

In certain embodiments, the present invention can employ monoclonal or polyclonal nucleotide-based aptamers. A "monoclonal nucleotide-based aptamer" as used herein includes a single aptamer with a known nucleotide sequence. A "polyclonal nucleotide-based aptamer" as used herein includes a population of aptamers with the same or different nucleotide sequences that all have an affinity for the same target molecule.

In other embodiments, an aptamer of this invention can be a recombinant protein or peptide that has been selected for specific binding to a target molecule according to methods known in the art (see, e.g., Hoppe-Seyler, Crnkovic-Mertens et al. 2004). The peptide-based aptamer can be a short peptide domain inserted into a supporting protein scaffold that enhances both specificity and affinity by conformationally constraining the peptide sequence (Colas, Cohen et al. 1996; Cohen, Colas et al. 1998; Buerger, Nagel-Wolfrum et al. 2003). In some embodiments of the present invention employing a peptide-based aptamer, the term "peptide-based aptamer" can be used to designate the peptide in the scaffold protein while the term "peptide" can refer to the inserted sequence.

In the methods of the present invention employing peptide-based aptamers, assays similar to the immunoassays described herein can be carried out to detect and/or quantify a biomarker of this invention, whereby a peptide-based aptamer is used in place of an antibody and an aptamer/target molecule complex, rather than an antibody/antigen complex is detected. The immunoassays described herein can also be adapted to employ an oligonucleotide-based aptamer in place of an antibody, for the detection of a nucleic acid/target molecule complex. In some embodiments, the immunoassays of this invention can also be modified to employ both aptamers and antibodies to detect and/or quantify a biomarker of this invention. Modification of any known immunoassay to accommodate the detection of binding of a nucleotide- or peptide-based aptamer to a target molecule would be well known to one of ordinary skill in the art.

As used herein, the term "signaling aptamer" includes aptamers with reporter molecules, such as a fluorescence dye, attached to the aptamer in such a way that upon conformational changes resulting from the interaction of the aptamer with a target molecule, the reporter molecule yields a differential signal, such as, for example, a change in fluorescence intensity. Alternatively, the amount of target molecule present may be quantified by the direct binding and retention of a fluorescently tagged aptamer on a solid surface or by the binding of a fluorescently tagged aptamer that recognizes the aptamer or antibody that binds specifically to the target molecule, i.e. secondary fluorescence assay. Examples of signaling aptamers can be found, for example, in U.S. Pat. No. 6,706,481, the entire contents of which are incorporated by reference herein for the disclosure of aptamers, methods of making aptamers and/or methods of using aptamers.

The present invention is more particularly described in the Examples set forth below, which are not intended to be limiting of the embodiments of this invention.

EXAMPLES

Example 1

Fatigue Biomarker Index (FBI) Program

The basic premise of the research is that expression of relatively small proteins and peptides in a biological sample (e.g., in saliva) are regulated by changes in energy utilization and demand. Whether fatigue could be measured through monitoring of the chemical composition of the biological sample (e.g., saliva) was tested, as described below.

The fatigue biomarker index (FBI) was discovered in saliva samples obtained during a carefully controlled laboratory study conducted by an exercise physiologist. Eight amateur athletes were challenged in the study, with each participant completing two sessions of prolonged exercise separated by approximately two weeks. During each session, the participants were asked to walk on a treadmill and pedal a cycle for ten hours with short breaks to collect muscle, blood and saliva samples and to be questioned regarding the perceived difficulty of the exercise. Among those peptides that were relatively abundant, it was found that the ratio of two of them provided the best correlation to measure fatigue and other changes occurring during prolonged exercise. This ratio of these two peptides is the fatigue biomarker index (FBI).

Low Values of the FBI are Associated with Fatigue

FIG. 1 shows unequivocally that high values of the FBI are associated with low values of fatigue, whereas low values of the FBI are associated with high values of fatigue. In other words, as the participants became fatigued, their FBI decreased. The measure used, relative perceived effort (RPE), is the "gold standard" for measurement of fatigue in the exercise physiology community (See, e.g., sportsmedicine.about.com website; 2004 article by Quinn et al. entitled "Rating of perceived exertion scale"). Basically, a subject is explained the scoring system prior to the start of exercise and then asked to score his/her perceived effort subsequently. Scores of 11 and 12 are associated with "light" effort whereas scores of 13 are associated with a "hard effort. A score of 19 is associated with an effort that is unsustainable. The solid bars in the middle of the boxes in FIG. 1 show the median value. The data shown establish that the FBI can be used to measure fatigue. It is important to note that the FBI is on a log scale and therefore the difference in FBI between rested and fatigued individuals is 2-3 orders of magnitude.

The FBI Changes in the Same Way, Time after Time

Figure 2:
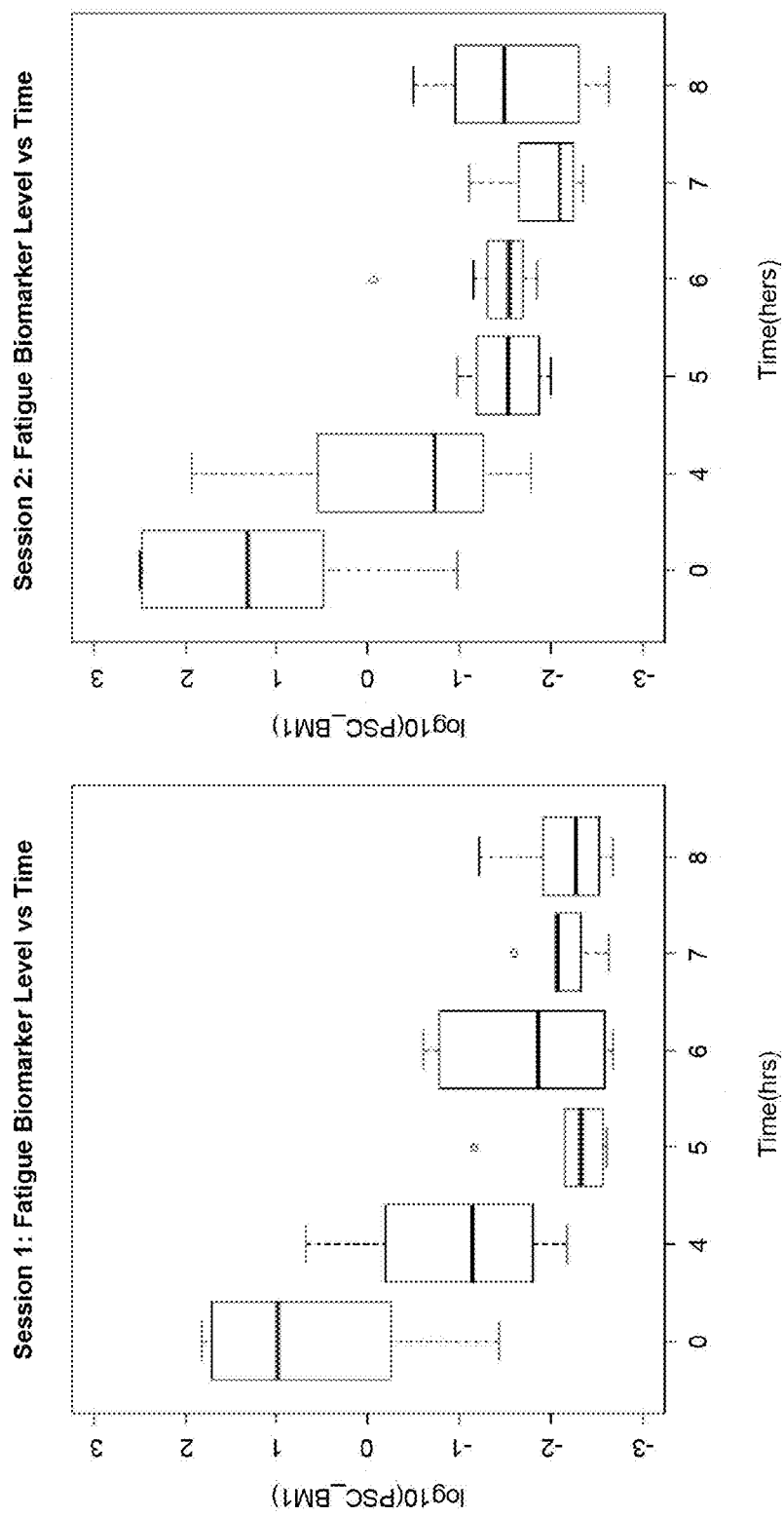
FIG. 2. Biomarker index levels return to baseline during recovery from fatigue. FBI levels returned to baseline levels during a cross-over study of physiological effects of endurance exercise. Data collected from two different training sessions are shown in separate panels. The same subjects participated in both sessions and for each session, the biomarker index levels for the entire group are shown as a function of time. At each time point, the solid black line is the group median. The hollow box around the solid black line indicates the bounds of the data from the first to the third quartile. A comparison of the values at time=0 and time=8 hrs within a session for either session shows they are significantly different, suggesting that the subjects became fatigued over the 8 hrs of a single session. However, the values at time=0 hrs for both sessions are nearly identical, indicating that whatever changes took place during the 8 hrs of one session were reversed by the start of the next session, i.e., the subjects recovered.

The initial discovery experiment also provided information on how the FBI changed during exercise and revealed that the FBI recovers and behaves similarly time after time. The eight subjects were asked to participate in a primary study and then to participate again two weeks later. The crossover study design was used to evaluate the impact of feeding participants carbohydrates or placebo after four hours of exercise (see, e.g., Harger et al. "Exogenous carbohydrate spares muscle glycogen in men and women during 10 h of exercise" *Medicine & Science in Sports & Exercise* pp. 2171-2179 (2007)). Median FBI values and corresponding quartiles are shown in FIG. 2. This figure shows that the FBI response of individuals is very similar from week to week and from time point to time point, indicating that the FBI is a good way of objectively measuring physical performance capability over long periods of time. In addition, this indicates that the FBI could be a good tool for optimizing performance capability over a period of months or years. Again the FBI is shown as changing over nearly three orders of magnitude from the beginning of the exercise regimen to the end. Moreover, with a recovery period of two weeks, the participants' median FBI returned to a value consistent with a non-fatigued state. It was also noted that no significant difference was found between carbohydrate vs. no carbohydrate treatment.

The FBI is Associated with Physical Performance Capability

Figure 3:
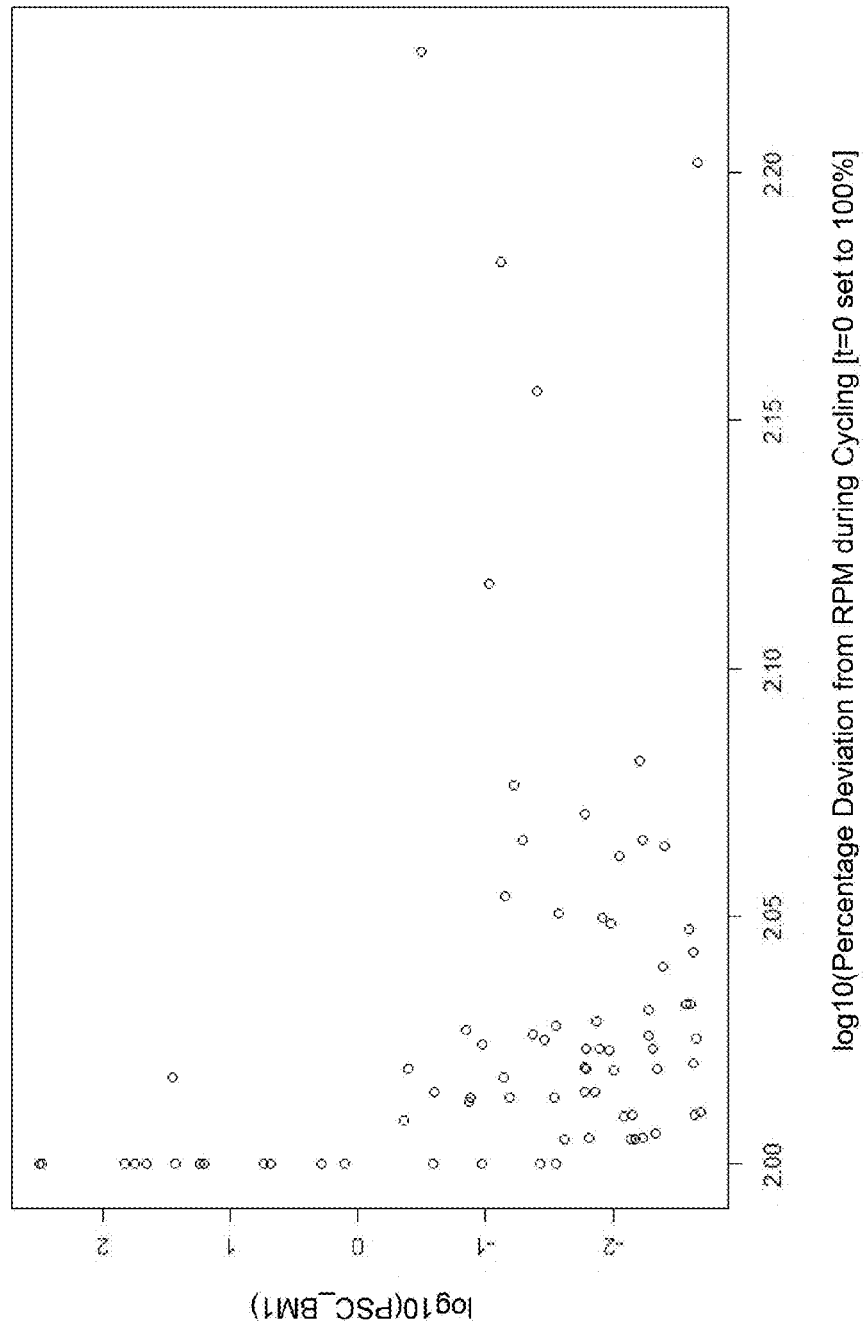
FIG. 3. Biomarker index levels decreased as deviation from expected performance increased. FBI levels decreased when cyclists deviated more from their expected level of performance in a controlled study of cycling. (Pearson's product-moment correlation, Correlation coefficient: −0.2127728, p-value: 0.03019, alternative hypothesis: true correlation is not equal to 0.)

Physical performance capability can be measured in a variety of ways. In the initial discovery experiment, physical performance capability was measured by evaluating the ability of the subjects to pedal at a constant rate for several minutes. As subjects became more fatigued, they were less able to pedal at a constant rate and instead pedaled much slower or faster. Thus, a measure of physical performance is the deviation from a target rate of pedaling. These data, shown in FIG. 3, demonstrate that a large deviation from the target rate was associated with reduced values of FBI, and thus greater fatigue. This finding supports the use of the FBI to evaluate an individual's physical performance capability.

Baseline FBI Predicts Success in the Special Operations Forces (SOF)

SOFs are elite and highly trained members of the US military. To be eligible for SOF, the candidate must be able to satisfy requirements for physical and mental agility and toughness. Having passed this initial hurdle, SOF candidates are then subjected to an indoctrination period for several months that involves extremely challenging training and evaluation. Only about 25% of SOF candidates pass this arduous indoctrination. The low success rate has been a problem in recent years because the numbers of new entrants do not make up for loss of experienced SOF members. Thus, there is a need and great interest on the part of SOFs to find ways of identifying if failing candidates can be brought up to standard through simple interventions and training. The FBI is a useful tool for this purpose.

Figure 4:
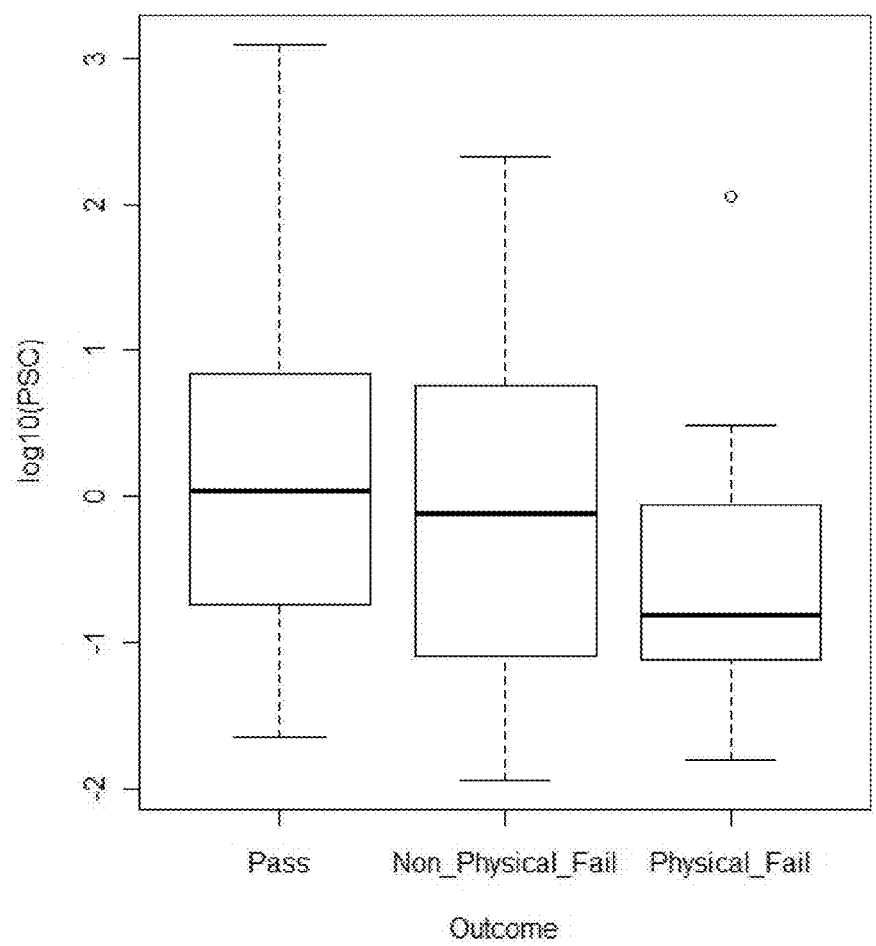
FIG. 4. Decreased levels of biomarker index associated with Special Operations Forces (SOF) candidate failure for physical reasons. FBI levels were lower in SOF candidates who failed training due to reasons related to physical performance (failed physical performance requirement or medical problem) compared to SOF candidates who passed training or who failed for reasons not related to physical performance (failed academic test, administrative discharge, decision to quit). (Kruskal-Wallis H test: p-value=0.03962.)

During a recent study, 85 SOF candidates were evaluated to identify demographic, physical performance, psychological and other factors affecting success. The FBI of an initial baseline saliva sample, taken before the start of the training and evaluation period, was found to be highly predictive of failure. SOF candidates can fail to succeed for a number of reasons, including poor academic performance, discipline issues and medical problems. As shown in FIG. 4, low values of the FBI were clearly associated with the inability to meet required standards for physical performance. Comparison of the FBI values observed for candidates failing for reasons related to physical performance with those taken from the other discovery experiment sets suggest that candidates failing for reasons related to physical performance have lower baseline levels of FBI.

Example 2

Discovery of the Fatigue Biomarker Index

Sample Collection and Liquid Chromatography-Mass Spectrometry (LC-MS) Analysis

Sample Collection

Saliva samples collected at t=0, 4, 5, 6, 7 and 8 hrs were first stored at −80° C. at the site of collection (University of Montana, Missoula) and later shipped on dry ice to another site (Hyperion Biotechnology, San Antonio, Tex.) for analysis. Samples were thawed and analyzed for small-molecular-weight biomarkers as described in the following sections. Each sample consisted of approximately 3 ml of saliva.

Protein Content

The level of protein in each saliva sample was quantified using the colorimetric bicinchoninic assay (BCA). Absorbance measurements (562 nm) and standard solutions were used to construct a calibration curve and linear regression was used to determine the final protein concentration for the unknown sample.

Size-Based Centrifugal Filtration

Raw saliva samples were sequentially spun through two different size-based centrifugal filters (Microcon, Millipore) with nominal sieve sizes of 50 kDa and 10 kDa. The 50 kDa filter was spun at 4,000 g at 4° C. for approximately 2.5 hours while the 10 kDa filter was spun at 10,000 g at room temperature for approximately 45 minutes.

Concentrating Samples

The filtrate from the 10 kDa filter was loaded onto a peptide trap column (C8, Michrom) and eluted in approximately 200 µL of elution buffer. The eluted sample was then dried using a heated vacuum chamber (Centrivap, Labconco).

Mass-Specific Labeling of Primary Amines

The dried sample was resuspended in a mixture of triethylammonium bicarbonate/ethanol (50 mM TEAB, final concentration) and acetic anhydride/ethanol (1:250 dilution). The TEAB/EtOH and acetic anhydride/EtOH solutions were prepared separately and then mixed (200 µl+20 µl, resp.). For the acetic anhydride, both 'light' (methyl protons) and 'heavy' (methyl deuterons) forms were used to allow mass-specific labeling of samples. The samples were incubated on a rotating platform for one hour at 37° C., after which the labeled samples were then dried again (Centrivap) and resuspended in LC-MS grade water with 0.1% acetic acid.

Liquid Chromatography

Small molecular weight components in saliva were separated using a liquid chromatography system (Waters ACQUITY) equipped with a C18 column (Acquity HPLC, BEH300 C18, 1.7 µm particle, 2.1×100 mm, Waters). Proteins and peptides were eluted using a linear gradient of water and methanol, spiked with 0.1% acetic acid to aid ionization during the subsequent analysis by mass spectrometry. The gradient was run from 90 to 65% water over 20 minutes.

Ion-Trap Mass Spectrometry Detection

Eluent from the LC system was injected directly into the electrospray ionization chamber of an ion-trap mass spectrometer (Esquire 3000+, Bruker, Billerica, Mass.). To optimize detection of small molecular weight peptides, the mass spectrometer was configured for detection of cations in the "Standard Detection" mode. Raw data files were exported in the ASCII format and then analyzed using software written in-house for the identification of potential biomarkers.

Analysis of LC-MS Data

Overview

Custom data analysis software (64-bit LabVIEW, National Instruments, Austin, Tex.) was written that used consistent and objective criteria to identify potential biomarkers. Specifically, the software used multiple stages of analysis, allowing the user to apply increasing levels of stringency at each stage to reduce lists of candidates from hundreds of thousands to less than one hundred. Moreover, as explained below, the user configured the exact level of stringency at each stage by adjusting several key parameters.

Identifying Peaks in a Single LCMS Dataset: Low Stringency

Initially, LCMS peaks were identified using peak width and peak intensity as selection criteria. Setting a low threshold for peak intensity ensured that every potential biomarker was identified but sacrificed analysis rate. The resulting list of peak coordinates (m/z, retention time) was large, often numbering more than 100,000. While a large number of these peaks would not lead to biomarker candidates, the later stages of analysis removed most of the irrelevant peaks while ensuring that every true biomarker candidate was evaluated.

Identifying Analytes Labeled with Mass-Specific Tags: Moderate Stringency

Figure 5:
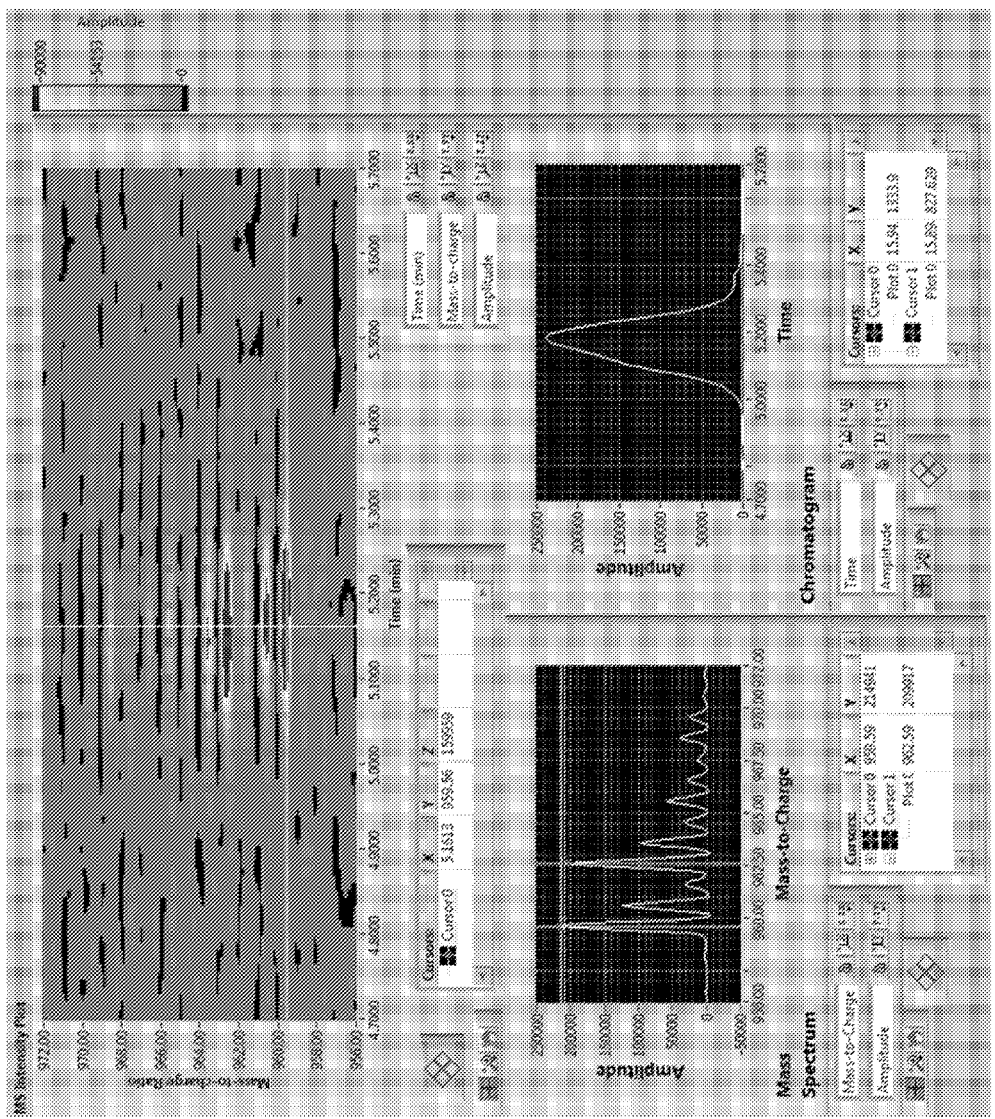
FIG. 5. A Pair of Mass Peaks with Spacing Predicted for Acetylation. Two aliquots from a single saliva sample were labeled independently with either light or heavy acetic anhydride, then mixed and analyzed by LC-MS. The region of interest shown above reveals two prominent peaks of similar intensity separated by a difference of 3 m/z units (959.59 and 962.59). The similarity of the peak intensities confirms similar levels of labeling in the independent reactions. As expected, the retention time for the deuterated species was slightly shorter than the retention time for the protonated species. The custom-written analysis software searched LC-MS runs for pairs of mass peaks with the predicted mass differences for acetic anhydride labeling, e.g., 1.5, 3, 6 and 9.

Biological fluids are chemically complex mixtures including ions, lipids, sugars, peptides, proteins and small molecules. To target the analysis toward peptide biomarkers, isotopes of acetic anhydride were used to label the free amines found on nearly all peptides. To identify acetylatable components of the sample, two aliquots from a single sample were labeled separately with light and heavy isotopes of acetic anhydride and then recombined for LCMS analysis. Acetylated ions appeared as pairs of peaks in the resulting LCMS data set, as illustrated in FIG. 5.

To identify peak pairs, the analysis software allowed the user to enter target mass differences as well as tolerances for m/z and retention time to account for noise and to control the stringency of the selection. The number of peak pairs identified in each sample was typically less than 30% of the entire number of peaks identified.

Figure 6:
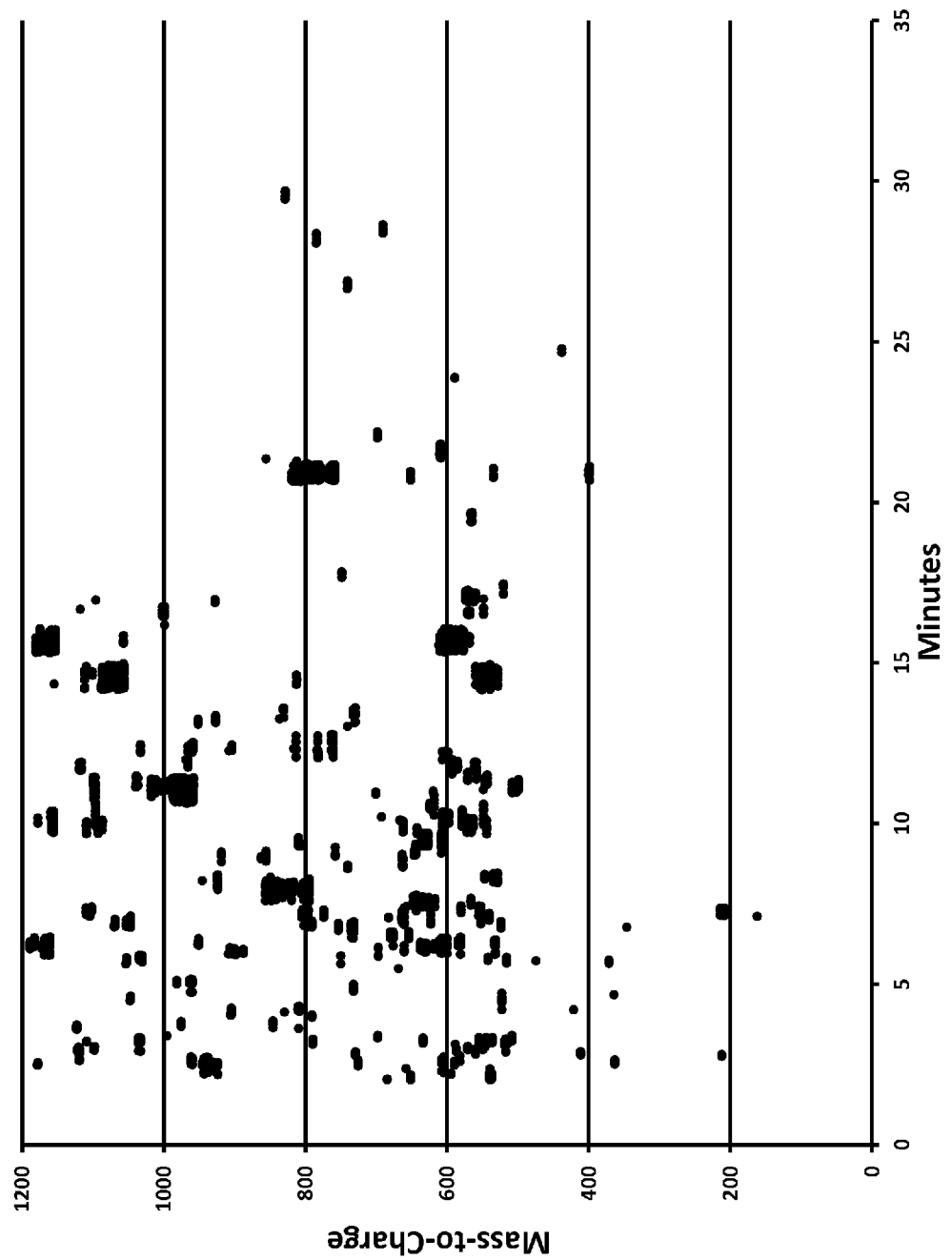
FIG. 6. Clustering of Peak Pairs. Saliva was collected simultaneously from eight individuals. Saliva samples were stored, processed and analyzed separately. Peaks identified in the eight LC-MS runs were analyzed for clusters of mass-peak pairs using a threshold of 60%. The plot shows the coordinates of the peak pairs found in common.

Cluster Analysis Identifying Peak Pairs Common to a Group of Samples: High Stringency After identifying all of the peak pairs within a single sample, the software then determined which peak pairs were common to a particular set of samples. For example, the software determined which peak pairs occurred in samples collected at baseline from study participants (e.g., before endurance exercise) and which peak pairs occurred in samples collected from the same study participants at some later time (e.g., after endurance exercise). The user set a minimum cluster size, expressed as a fraction, which indicates the fraction of participants that must have a particular pair of peaks in common before it was added to the final list of peak coordinates. A high fraction (>50%) introduced a high level of stringency to the analysis, reducing peak lists that initially contained hundreds of thousands of coordinates to lists that contained a few hundred coordinates. An example of the results from this cluster analysis is shown in FIG. 6.

Identifying Potential Biomarkers: High Stringency

Cluster analysis results were compared among individuals from different study groups and among samples collected at a minimum of two different time points. For example, the cluster map extracted from the baseline data was compared with the cluster map extracted after eight hours of continuous exercise. Differences in these maps revealed the coordinates for potential biomarkers. Peak intensities were then quantified for all files using the coordinates of potential biomarkers and statistical tests were performed to determine whether peak intensity differences were significant.

Peak Intensity Ratios as Unitless Biomarker Indices

Quantifying LCMS data is challenging, leading to the use of ratios of peak intensities as unitless biomarker indices instead of absolute intensity levels for single ions. By calculating a ratio, the likelihood was reduced that any observed difference arose from trivial sources such as matrix effects, differences in the amount of protein injected, variation in ionization efficiency, etc.

Separation of Peaks of Interest

After analyzing the statistical significance of intensity differences for peaks of interest, a standard fraction collector (Fraction Collector III, Waters) was used to isolate LC fractions (30 s wide) rich in those molecules with statistically significant different intensities. Fractions collected from similar times of multiple LC-MS injections were combined and sent frozen on dry ice for analysis at a high-resolution mass spectrometry facility (University of Illinois, Champaign-Urbana).

High-Resolution Mass Spectrometry

Peptide sequences were determined using data collected on a high-resolution mass spectrometer (12T LTQ-FT Ultra, Thermo Scientific, Waltham, Mass.). For the nominally 700.4 m/z species, sample was infused into the mass spectrometer using an automated injector (TriVersa Robot, Advion, Ithaca, N.Y.). An aliquot (7.5 µl) of sample sent from Hyperion Biotechnology was mixed 1:1 with 1:1 MeOH/$H_2O$ (7.5 µl) and formic acid (0.3 µl). For the nominally 758.4 m/z species, the sample (15 µl) was concentrated using a commercially available reverse phase column (C18 ZipTip, Millipore, Billerica, Mass.). Sample was eluted using acetonitrile/water/acetic acid (77/22/1, 5 µl). Eluent was added to 1:1 MeOH/$H_2O$ (7.5 µl) and formic acid (0.3 µl). Data were collected for both intact and fragmented species. Mass spectra were analyzed with ProSightPC.

Results

Figure 7:
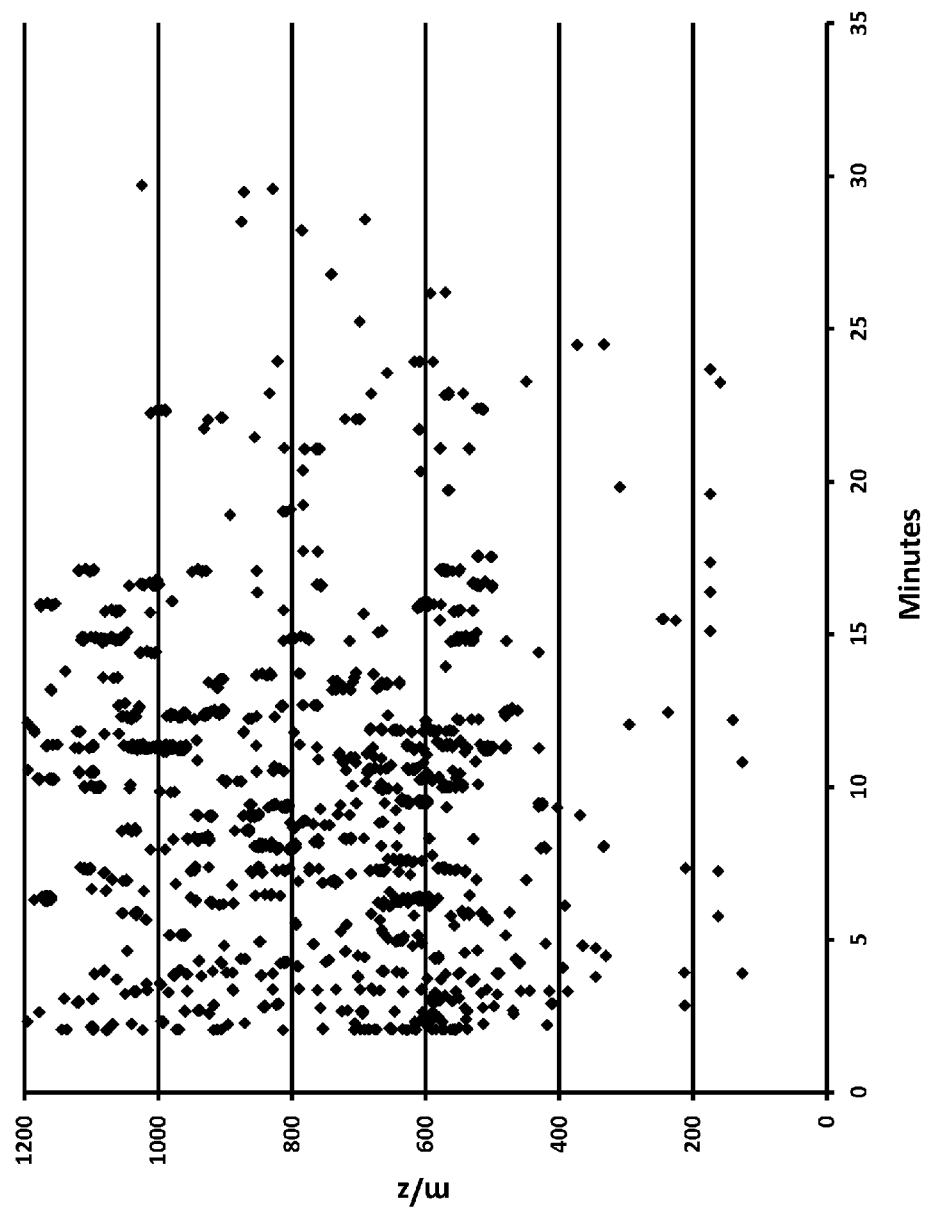
FIG. 7. Distribution of Mass Peak Pairs in One Saliva Sample. Here, we display the time and mass-to-charge ratio for those peak pairs that have an expected mass difference for a pair of ions labeled with light and heavy acetic anhydride.

Saliva samples were collected and analyzed as described above. The resulting LC-MS runs were analyzed with custom-written software, which enabled searches for clusters of mass-peak pairs within each set of data, e.g., clusters of peaks that appeared in a majority of the participant's samples collected at time=0 or time=8 hrs. Each LC-MS run was evaluated using the LabVIEW application and a list of detected mass pairs was written to a text file. In a typical LC-MS run, hundreds of thousands to millions of peaks were detected, of which several thousand were separated by one of the expected mass differences. FIG. 7, shows plotting for one LC-MS run all of the peak pairs which had one of the expected mass differences.

Figure 8:
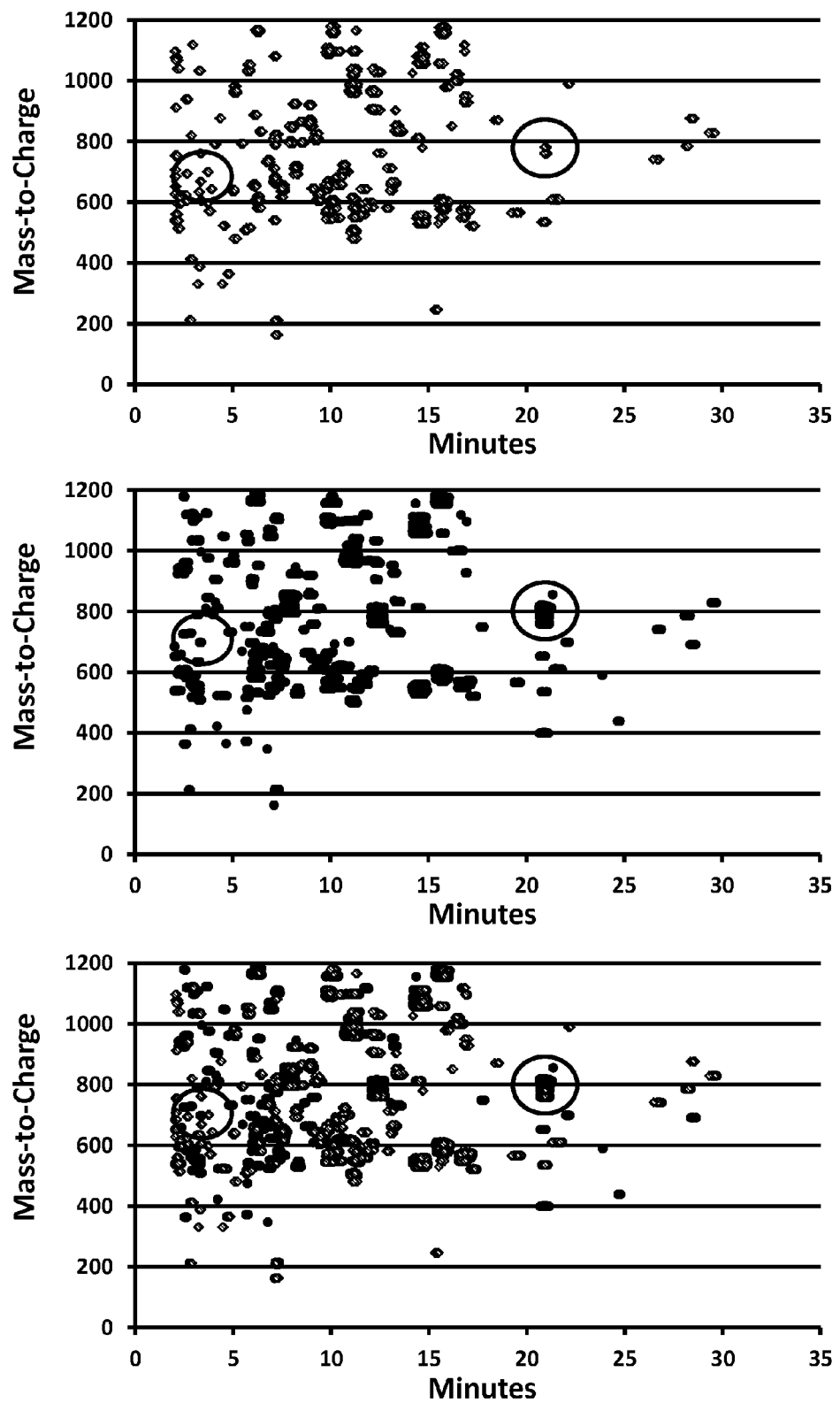
FIG. 8. Clustering of Peak Pairs. The eight LC-MS runs taken at time=0 and time=8 hrs were analyzed separately for clusters of mass-peak pairs using a threshold of at least five points within the cluster. The three panels show the following: Top—time=0 hrs, Middle—time=8 hrs and Bottom—overlay of time=0 hrs and time=8 hrs. Black—time=0 hrs and Grey—time=8 hrs.

The data set from this study was further analyzed by identifying those mass peak pairs that occurred more than five times among the eight LC-MS runs. For this analysis, a custom-written program calculated the dimensions of an ellipse centered on each mass-peak pair with a major axis along the time axis and a minor axis along the mass axis. Typical dimensions were 0.3 minutes along the major axis and 0.1 m/z units along the minor axis. All peaks falling within the ellipse around each point were counted as "neighbors" and those points with more than four neighbors were plotted in FIG. 8.

From this plot of clusters, sites of potential biomarkers were identified, i.e., those sites for which a cluster appeared in one map, but not in the other map. Two such sites are highlighted in the maps shown in FIG. 8. The signals from these sites led to the identification of a biomarker associated with the physiological changes that accompany prolonged periods of physical activity. In the tables below, this biomarker is referred to as the Fatigue Biomarker Index (FBI). However, before presenting the data for this biomarker in the current study of BMTs, a description is provided of how the intensity of this biomarker index was calculated.

Quantifying Data Collected in an Ion Trap Mass Spectrometer

Figure 9:
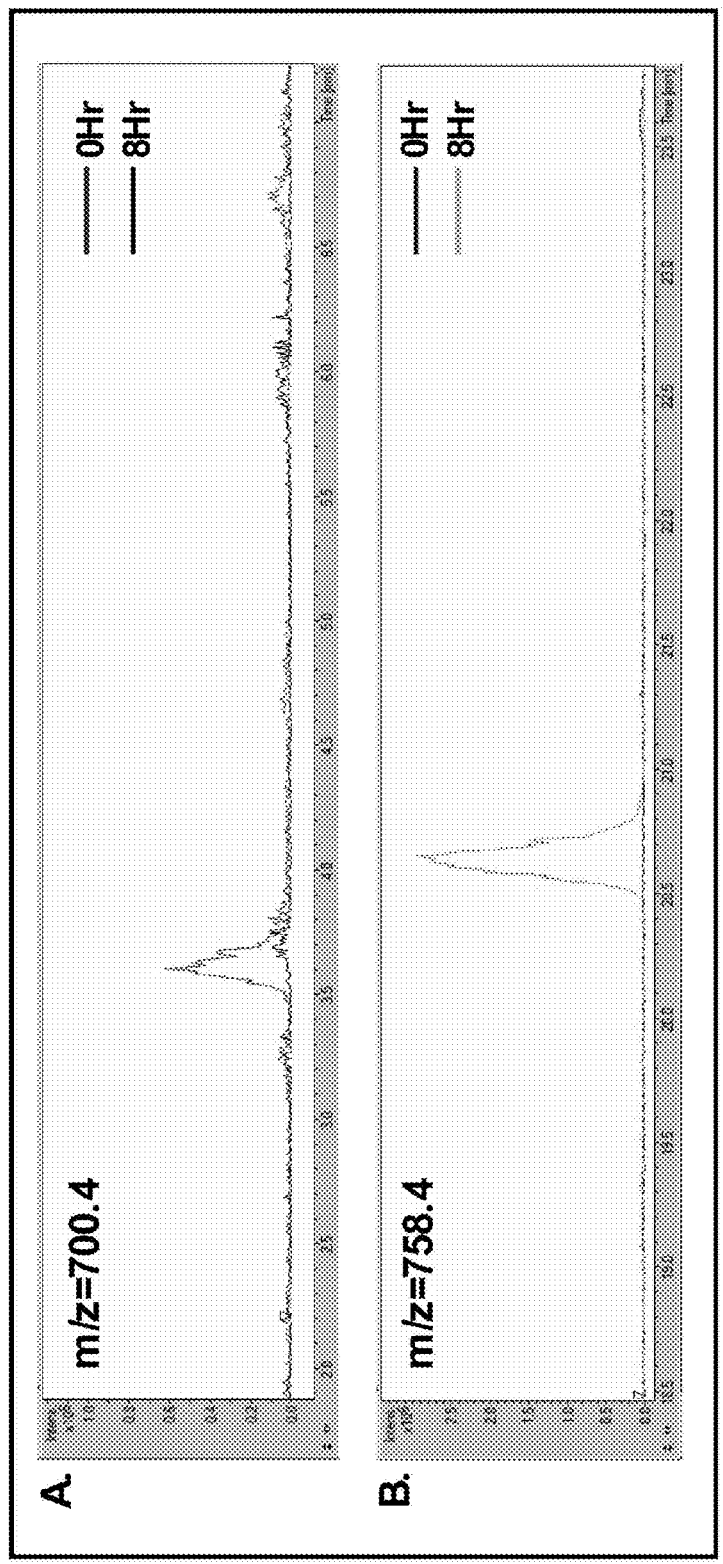
FIG. 9. Identifying the Components of a Biomarker Index. Representative data are shown for the two components used to calculate the Fatigue Biomarker Index (FBI). The traces in panel A are for the ion with a mass-to-charge ratio (m/z) of 700.4 and a retention time of ~3.6 min and the traces in panel B are for the ion with m/z=758.4 and a retention time of ~20.6 min. The FBI is calculated as the ratio of the intensities at these two locations ($I_{700.4}/I_{758.4}$). The resulting index is a unitless parameter. Results for all participants in Harger-Domitrovich's study are shown in Tables 1 & 2.

The signal intensity detected by an ion trap mass spectrometer is influenced by a large number of factors including the concentration of the analyte, the ability of the molecule in solution to free itself of solvent, the flow rate of the solution through the electrospray needle, the total amount of protein injected in the sample and the distribution of atomic ions such as calcium and sodium. The large number of influencing factors makes quantification of ion-trap data challenging, if not impossible. Therefore, when determining whether a difference in ion intensity in one set of data represents a true change in concentration compared to the ion intensity in another set of data, it is important to consider carefully how signals are normalized so that only true differences are identified. For the purposes of the study, the following approach for identifying biomarkers has been used. Two LC-MS peaks, i.e., points specified by both time and mass-to-charge ratio which have been identified which have changed independently in intensity. Importantly, the direction of change for one of these ions is OPPOSITE the direction of change for the other ion, i.e., one ion decreases in intensity while the other ion increases in intensity when comparing the data collected at time=0 and time=8 hrs. Examples of these changes are shown for both of these ions in FIG. 9.

High-Resolution Mass Spectrometry Data

Figure 10:
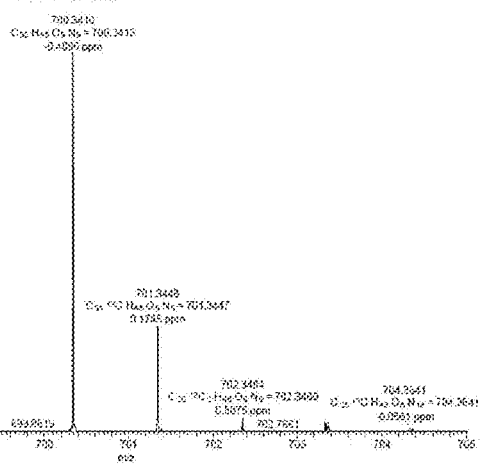
FIG. 10. High-resolution Mass Spectrometry Data. Mass spectrometry data for intact and fragmented samples are shown. For both parent ions, the intact mass matches to theoretical mass of the peptide within 0.5 ppm and fragmentation data support the sequences provided.
Figure 10:
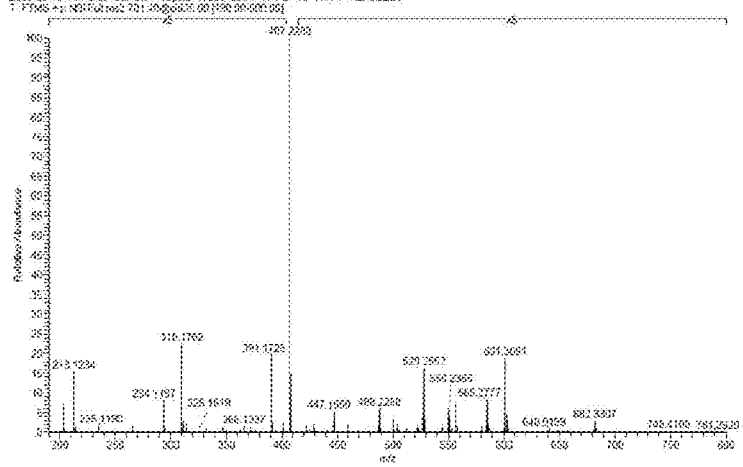
Figure 10:
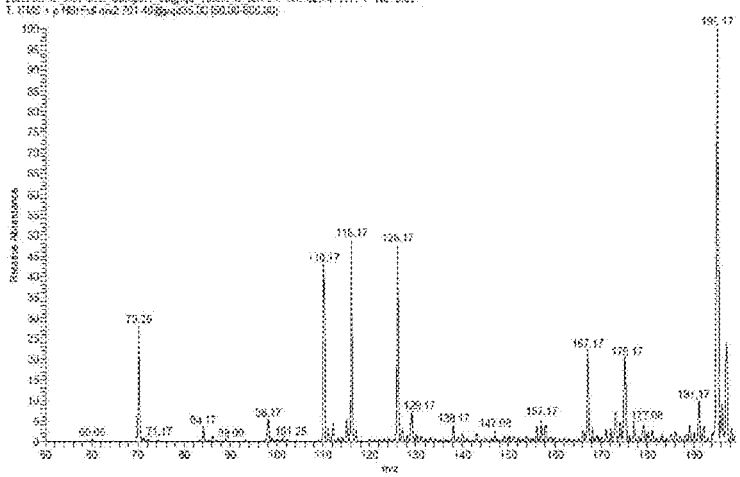
Figure 10:
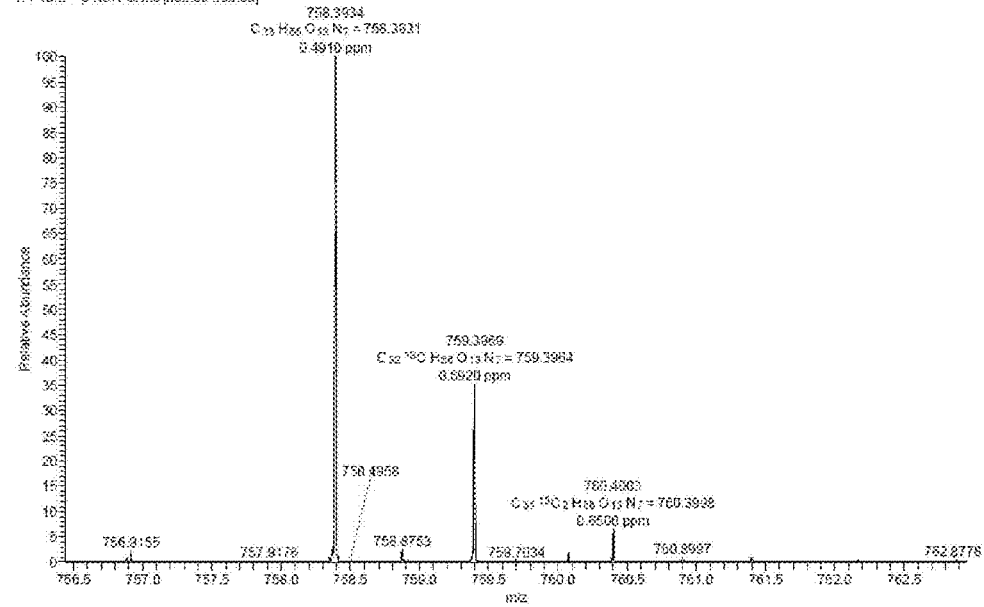
Figure 10:
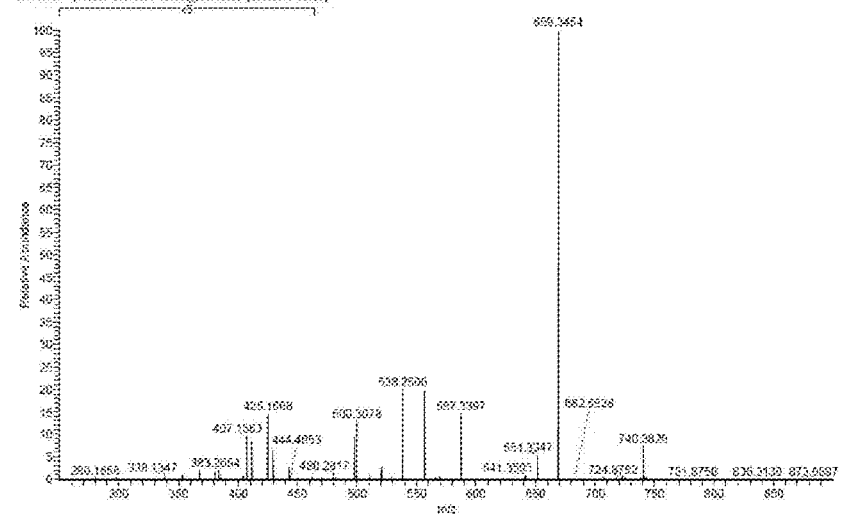
Figure 10:
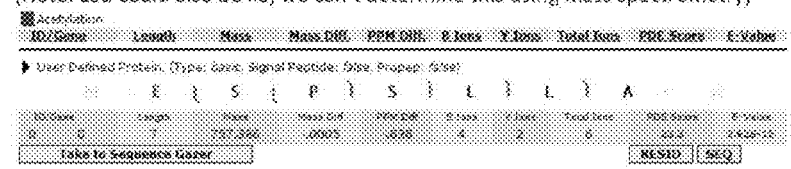

Amino acid sequence data for the two peptide components of the FBI were obtained at a high-resolution mass spectrometry site (University of Illinois, Champaign-Urbana, Neil Kelleher & Paul Thomas). Briefly, the high-resolution analysis returned the following sequences for the two peptides using the single-letter amino acid notation: (1) Acetyl-G-G-H-P-P-P-P (SEQ ID NO:1) and (2) Acetyl-E-S-P-S-L-L-A (SEQ ID NO:2). Raw data are shown in FIG. 10. In the second sequence, it is important to note that the two L residues can be either I or L, as these residues are isobaric and cannot be distinguished by mass-to-charge ratio. To determine the true amino acid type at the fifth and sixth positions of the second peptide, a publicly available database of bioinformatic information (National Center for Biotechnology Information) was searched for potential sequences, i.e., E-S-P-S-L-L-A (SEQ ID NO:3), E-S-P-S-L-I-A (SEQ ID NO:2), E-S-P-S-I-L-A (SEQ ID NO:4) or E-S-P-S-I-I-A (SEQ ID NO:5). Only one of these sequences, E-S-P-S-L-I-A (SEQ ID NO:2), is found in the consensus sequence of human genes. The genes containing the sequences G-G-H-P-P-P-P (SEQ ID NO:1) or E-S-P-S-L-I-A (SEQ ID NO:2) are described below.

Genetic Information for Proteins Containing the Sequence of FBI Component Peptides The Proline-rich Salivary Proteins (PRPs) constitute up to 70% of the soluble protein found in human saliva, and homologous proteins have been reported in non-human primates as well as in other animals, including rats, mice and hamsters. In humans, PRPs are the products of two gene families located on chromosome #12: (i) the HaeIII family, comprising two almost identical genes, PRH1 and PRH2, which code for acidic PRPs, and (ii) the BstN1 family, which includes four genes (PRB1, PRB2, PRB3 and PRB4) and codes for basic PRPs. With post-transcriptional and post-translational processing, these six genes are responsible for at least thirteen different human protein products. In addition, a number of allelic forms, representing minor changes in amino acid composition, have also been identified for each of these genes. A variety of functions have been suggested for PRPs in saliva including protection against bacterial pathogens, regulation of calcium phosphate deposition, and most recently as a protective mechanism against dietary tannins and other phenolic compounds.

The fatigue biomarker with the sequence GGHPPPP (Peptide #1, SEQ ID NO:1) is derived from one (or possibly both) of the PRH genes as a primary translation product containing 166 amino acids (see FIG. 11, SEQ ID NO:6, for details of PRP protein sequence). Because the sequences specifying Peptide #1, as well as the flanking sequences, are identical in each of these genes, it is not possible at this time to distinguish the specific chromosomal source of the peptide. Processing of the primary translation product removes a 16-amino acid signal peptide from the amino terminus of the protein, resulting in the 150 amino acid Salivary Acidic Protein 1/2. Further modification removes an additional 44 amino acids from the carboxyl terminus, yielding the 106 amino acid, Salivary Acidic Protein 3/4. Peptide #1 spans amino acid residues 82-88 in each of these proteins (98-104 of the primary translation product). The method of release of Peptide #1 into saliva is unclear. A detailed search of well-characterized proteases did not reveal any with enzymatic specificities that would generate this peptide fragment from the larger proteins. However, a recent report identifies a number of peptide fragments in this size range that are apparently generated from PRPs by unknown proteases present in whole saliva.

The fatigue biomarker peptide with the sequence ESPSLIA (Peptide #2, SEQ ID NO:2) derives from one, or perhaps both, of a pair of the basic proline-rich protein genes, PRB1 and PRB2 (SEQ ID NO:8), which are closely linked to the PRH genes. These two genes code for primary translation products of 392 (PRB1, SEQ ID NO:7) and 416 (PRB2, SEQ ID NO:8) amino acids (see FIG. 11 for details). Removal of the signal peptide produces Basic Salivary Proline-rich Protein 1 and Basic Salivary Proline-rich Protein 2, and further modifications yield several smaller products from each protein. Two of the final products of the PRB1 gene (Basic Salivary Proline-rich Protein 1 and Proline-rich Peptide II-2) and one from the PRB2 gene (Basic Salivary Proline-rich Protein 2) contain Peptide #2. In each of these, the peptide spans amino acid residues 11-17 (27-33 of primary translation product). As with Peptide #1, it is as yet unclear whether only one or both of the PRB1 and PRB2 genes is the source of Peptide #2.

The above examples clearly illustrate the advantages of the invention. Although the present invention has been described with reference to specific details of certain embodiments thereof, it is not intended that such details should be regarded as limitations upon the scope of the invention except as and to the extent that they are included in the accompanying claims.

Throughout this application, various patents, patent publications and non-patent publications are referenced. The disclosures of these patents, patent publications and non-patent publications in their entireties are incorporated by reference herein into this application in order to more fully describe the state of the art to which this invention pertains.

REFERENCES

Azen E A. "Genetics of Salivary Protein Polymorphisms" *Critical Reviews in Oral Biology and Medicine* 4:479-484 (1993)

Minaguchi K and Bennick A. "Genetics of Human Salivary Proteins" *Journal of Dental Research* 68:2-15 (1989)

Kim H and Maeda N. "Structures of Two HaeIII-type Genes in the Human Salivary Proline-rich Protein Multigene Family" *Journal of Biological Chemistry* 261:6712-6718 (1985)

Carlson D M. "Salivary Proline-rich Proteins: Biochemistry, Molecular Biology and Regulation of Expression" *Critical Reviews in Oral Biology and Medicine* 4:495-502 (1993)

Messana I, et al. "Trafficking and Postsecretory Events Responsible for the Formation of Secreted Human Salivary Peptides" Molecular *and Cellular Proteomics* 7:911-926 (2008)

Table 1 summarizes the FBI data for the participants in the study by Harger-Domitrovich et al.

TABLE 1

Levels of PSC_BM1 in Participants in a Study of Ultraendurance Exercise. Data collected from the participants in a study of ultraendurance exercise are summarized. The average value at time = 0 is significantly different from the average value at t = 8 hrs based upon a paired samples t-test (p < 0.05). See Appendix 2 for a complete description of the values used in computing this table.

| Participant | FBI (t = 0) | FBI (t = 8 hrs) |
|---|---|---|
| S2A | 56.4231 | 0.0022 |
| S3A | 0.0379 | 0.0049 |
| S4A | 67.7590 | 0.0122 |
| S5A | 1.2766 | 0.0609 |
| S6A | 17.2744 | 0.0059 |
| S7A | 45.6375 | 0.0022 |
| S8A | 0.2589 | 0.0040 |
| S9A | 5.4059 | 0.0127 |
| Avg. | 24.2592 | 0.0131 |
| St. Dev. | 27.9768 | 0.0197 |

Table 2 provides the raw and processed data related to the discovery of the FBI.

TABLE 2.1

Raw Data Used in the Discovery of FBI.

| Participant | Mass-to-charge Ratio | Time | Intensity | Mass-to-charge Ratio | Time | Intensity | Normalized Intensity ($I_{700}/I_{758}$) |
|---|---|---|---|---|---|---|---|
| S2A(0) | 758.59 | 21.7 | 1600 | 700.39 | 3.7 | 90277 | 56.4231 |
| S3A(0) | 758.39 | 21.2 | 237669 | 700.39 | 3.7 | 9017 | 0.0379 |
| S4A(0) | 758.19 | 21.8 | 1195 | 700.39 | 3.8 | 80972 | 67.7590 |
| S5A(0) | 758.69 | 21.1 | 72923 | 700.59 | 3.8 | 93096 | 1.2766 |
| S6A(0) | 758.39 | 20.8 | 492 | 700.49 | 3.7 | 8499 | 17.2744 |
| S7A(0) | 758.29 | 20.9 | 629 | 700.39 | 3.7 | 28706 | 45.6375 |
| S8A(0) | 758.69 | 21.0 | 51962 | 700.39 | 3.7 | 13451 | 0.2589 |
| S9A(0) | 758.49 | 20.9 | 12481 | 700.39 | 3.8 | 67471 | 5.4059 |
| Avg. | 758.47 | 21.2 | 47369 | 700.43 | 3.7 | 48936 | 24.2592 |
| St. Dev. | 0.18 | 0.4 | 81691 | 0.07 | 0.1 | 37657 | 27.9768 |

| Participant | Mass-to-charge Ratio | Time | Intensity | Mass-to-charge Ratio | Time | Intensity | Normalized Intensity ($I_{700}/I_{758}$) | 0 Hr/ 8 Hr |
|---|---|---|---|---|---|---|---|---|
| S2A(8) | 758.59 | 21 | 460000 | 700.39 | 3.7 | 1000 | 0.0022 | 25954.6 |
| S3A(8) | 758.39 | 21 | 294137 | 700.49 | 3.7 | 1438 | 0.0049 | 7.8 |
| S4A(8) | 758.69 | 21.1 | 147769 | 700.39 | 3.7 | 1809 | 0.0122 | 5534.9 |
| S5A(8) | 758.69 | 20.8 | 612407 | 700.49 | 4 | 37266 | 0.0609 | 21.0 |
| S6A(8) | 758.69 | 20.9 | 219816 | 700.69 | 3.7 | 1298 | 0.0059 | 2925.4 |
| S7A(8) | 758.69 | 20.9 | 700144 | 700.19 | 3.8 | 1566 | 0.0022 | 20404.1 |
| S8A(8) | 758.69 | 20.6 | 363869 | 700.59 | 3.7 | 1467 | 0.0040 | 64.2 |
| S9A(8) | 758.69 | 21 | 436891 | 700.39 | 3.8 | 5570 | 0.0127 | 424.0 |
| Avg. | 758.64 | 20.9 | 404379 | 700.45 | 3.8 | 6427 | 0.0131 | 6917.0 |
| St. Dev. | 0.11 | 0.2 | 188456 | 0.15 | 0.1 | 12547 | 0.0197 | 10327.4 |

The location, expressed as the mass-to-charge ratio and retention time, of the "light" isoform of the ion is reported for two peaks in each file: one centered near m/z = 758.5, $t_R$ = 21 mins and one centered near m/z = 700.5, $t_R$ = 3.8 mins. For each file, the peak intensity of the ion current at that location was recorded. Cumulative statistics (average and standard deviation) are presented at the bottom of each column. The upper table has data for the participants at t = 0 and the lower table has data from t = 8 hrs. The value in the last column of the lower table reports the fold change in the level of FBI from 0 Hr to the 8 Hr condition.

What is claimed is:

1. A method of guiding a human subject's physical training activity, comprising:
   a) measuring the concentration of each of two peptides, GGHPPPP (SEQ ID NO:1) and ESPSLIA (SEQ ID NO:2), in a saliva sample taken from the subject when the subject is in a rested state, wherein the subject is an adult athlete or an amateur athlete;
   b) identifying the subject's level of physical fatigue by calculating the ratio of the concentration of GGHPPPP (SEQ ID NO:1) to the concentration of ESPSLIA (SEQ ID NO:2) measured in (a) according to the equation:

Fatigue biomarker index (FBI)=[GGHPPPP]/ [ESPSLIA];

c) having the subject initiate or resume a physical training program comprising activities of different intensity;
   d) measuring the concentration of each of two peptides, GGHPPPP (SEQ ID NO:1) and ESPSLIA (SEQ ID NO:2), in a saliva sample taken from the subject at one or more time points after (c);
   e) identifying the subject's level of physical fatigue by calculating the ratio of the concentration of GGHPPPP (SEQ ID NO:1) to the concentration of ESPSLIA (SEQ ID NO:2) for each sample measured in (d) according to the equation:

Fatigue biomarker index (FBI)=[GGHPPPP]/ [ESPSLIA]; and f) guiding the subject's physical training program by modifying the intensity of subsequent activities using the last of the subject's ratio(s), as calculated in (e), such that a decrease in the ratio relative to the previous ratio leads to a subsequent decrease in the subject's training intensity, an increase in the ratio relative to the previous ratio leads to a subsequent increase in the subject's training intensity, and a constant ratio relative to the previous ratio leads to a subsequent constant level in the subject's training intensity.

2. The method of claim 1, wherein the physical training program is a military training program.

* * * * *

SEQUENCE LISTING

<160> NUMBER OF SEQ ID NOS: 8

<210> SEQ ID NO 1
<211> LENGTH: 7
<212> TYPE: PRT
<213> ORGANISM: Artificial
<220> FEATURE:
<223> OTHER INFORMATION: Biomarker peptide sequence

<400> SEQUENCE: 1

Gly Gly His Pro Pro Pro Pro
1               5

<210> SEQ ID NO 2
<211> LENGTH: 7
<212> TYPE: PRT
<213> ORGANISM: Artificial
<220> FEATURE:
<223> OTHER INFORMATION: Biomarker peptide sequence

<400> SEQUENCE: 2

Glu Ser Pro Ser Leu Ile Ala
1               5

<210> SEQ ID NO 3
<211> LENGTH: 7
<212> TYPE: PRT
<213> ORGANISM: Artificial
<220> FEATURE:
<223> OTHER INFORMATION: Hypothetical biomarker peptide sequence

<400> SEQUENCE: 3

Glu Ser Pro Ser Leu Leu Ala
1               5

<210> SEQ ID NO 4
<211> LENGTH: 7
<212> TYPE: PRT
<213> ORGANISM: Artificial
<220> FEATURE:
<223> OTHER INFORMATION: Hypothetical biomarker peptide sequence

<400> SEQUENCE: 4

Glu Ser Pro Ser Ile Leu Ala
1               5

<210> SEQ ID NO 5
<211> LENGTH: 7
<212> TYPE: PRT
<213> ORGANISM: Artificial
<220> FEATURE:
<223> OTHER INFORMATION: Hypothetical biomarker peptide sequence

<400> SEQUENCE: 5

Glu Ser Pro Ser Ile Ile Ala
1               5

<210> SEQ ID NO 6
<211> LENGTH: 166
<212> TYPE: PRT
<213> ORGANISM: Homo sapiens

<400> SEQUENCE: 6

Met Leu Leu Ile Leu Leu Ser Val Ala Leu Leu Ala Phe Ser Ser Ala
1               5                   10                  15

```
Gln Asp Leu Asn Glu Asp Val Ser Gln Glu Asp Val Pro Leu Val Ile
            20                  25                  30

Ser Asp Gly Gly Asp Ser Glu Gln Phe Leu Asp Glu Arg Gln Gly
        35                  40                  45

Pro Pro Leu Gly Gly Gln Gln Ser Gln Pro Ser Ala Gly Asp Gly Asn
 50                  55                  60

Gln Asp Gly Pro Gln Gln Gly Pro Pro Gln Gly Gly Gln Gln
 65                  70                  75                  80

Gln Gln Gly Pro Pro Pro Gln Gly Lys Pro Gln Gly Pro Pro Gln
                85                  90                  95

Gln Gly Gly His Pro Pro Pro Gln Gly Arg Pro Gln Gly Pro Pro
            100                 105                 110

Gln Gln Gly Gly His Pro Arg Pro Pro Arg Gly Arg Pro Gln Gly Pro
        115                 120                 125

Pro Gln Gln Gly Gly His Gln Gln Gly Pro Pro Pro Pro Pro Gly
 130                 135                 140

Lys Pro Gln Gly Pro Pro Gln Gly Gly Arg Pro Gln Gly Pro Pro
145                 150                 155                 160

Gln Gly Gln Ser Pro Gln
            165
```

<210> SEQ ID NO 7
<211> LENGTH: 392
<212> TYPE: PRT
<213> ORGANISM: Homo sapiens

<400> SEQUENCE: 7

```
Met Leu Leu Ile Leu Leu Ser Val Ala Leu Leu Ala Leu Ser Ser Ala
 1               5                  10                  15

Gln Asn Leu Asn Glu Asp Val Ser Gln Glu Glu Ser Pro Ser Leu Ile
            20                  25                  30

Ala Gly Asn Pro Gln Gly Pro Ser Pro Gln Gly Gly Asn Lys Pro Gln
        35                  40                  45

Gly Pro Pro Pro Pro Pro Gly Lys Pro Gln Gly Pro Pro Gln Gly Gly
 50                  55                  60

Gly Asn Lys Pro Gln Gly Pro Pro Pro Gly Lys Pro Gln Gly Pro
 65                  70                  75                  80

Pro Pro Gln Gly Asp Lys Ser Arg Ser Pro Arg Ser Pro Gly Lys
                85                  90                  95

Pro Gln Gly Pro Pro Gln Gly Gly Asn Gln Pro Gln Gly Pro Pro
            100                 105                 110

Pro Pro Pro Gly Lys Pro Gln Gly Pro Pro Gln Gly Gly Asn Lys
        115                 120                 125

Pro Gln Gly Pro Pro Pro Gly Lys Pro Gln Gly Pro Pro Pro Gln
 130                 135                 140

Gly Asp Lys Ser Gln Ser Pro Arg Ser Pro Pro Gly Lys Pro Gln Gly
145                 150                 155                 160

Pro Pro Pro Gln Gly Gly Asn Gln Pro Gln Gly Pro Pro Pro Pro
            165                 170                 175

Gly Lys Pro Gln Gly Pro Pro Pro Gln Gly Gly Asn Lys Pro Gln Gly
        180                 185                 190

Pro Pro Pro Pro Gly Lys Pro Gln Gly Pro Pro Gln Gly Asp Lys
                195                 200                 205

Ser Gln Ser Pro Arg Ser Pro Gly Lys Pro Gln Gly Pro Pro Pro
            210                 215                 220
```

```
Gln Gly Gly Asn Gln Pro Gln Gly Pro Pro Pro Pro Gly Lys Pro
225                 230                 235                 240

Gln Gly Pro Pro Gln Gly Gly Asn Arg Pro Gln Gly Pro Pro Pro
            245                 250                 255

Pro Gly Lys Pro Gln Gly Pro Pro Gln Gly Asp Lys Ser Arg Ser
        260                 265                 270

Pro Gln Ser Pro Pro Gly Lys Pro Gln Gly Pro Pro Gln Gly Gly
    275                 280                 285

Asn Gln Pro Gln Gly Pro Pro Pro Pro Gly Lys Pro Gln Gly Pro
290                 295                 300

Pro Pro Gln Gly Gly Asn Lys Pro Gln Gly Pro Pro Pro Gly Lys
305                 310                 315                 320

Pro Gln Gly Pro Pro Ala Gln Gly Gly Ser Lys Ser Gln Ser Ala Arg
        325                 330                 335

Ala Pro Pro Gly Lys Pro Gln Gly Pro Pro Gln Gln Glu Gly Asn Asn
            340                 345                 350

Pro Gln Gly Pro Pro Pro Ala Gly Gly Asn Pro Gln Gln Pro Gln
        355                 360                 365

Ala Pro Pro Ala Gly Gln Pro Gln Gly Pro Pro Arg Pro Pro Gln Gly
370                 375                 380

Gly Arg Pro Ser Arg Pro Pro Gln
385                 390

<210> SEQ ID NO 8
<211> LENGTH: 416
<212> TYPE: PRT
<213> ORGANISM: Homo sapiens

<400> SEQUENCE: 8

Met Leu Leu Ile Leu Leu Ser Val Ala Leu Ala Leu Ser Ser Ala
1               5                   10                  15

Gln Asn Leu Asn Glu Asp Val Ser Gln Glu Glu Ser Pro Ser Leu Ile
            20                  25                  30

Ala Gly Asn Pro Gln Gly Ala Pro Pro Gln Gly Gly Asn Lys Pro Gln
            35                  40                  45

Gly Pro Pro Ser Pro Pro Gly Lys Pro Gln Gly Pro Pro Gln Gly
    50                  55                  60

Gly Asn Gln Pro Gln Gly Pro Pro Pro Pro Gly Lys Pro Gln Gly
65                  70                  75                  80

Pro Pro Pro Gln Gly Gly Asn Lys Pro Gln Gly Pro Pro Pro Gly
                85                  90                  95

Lys Pro Gln Gly Pro Pro Pro Gln Gly Asp Lys Ser Arg Ser Pro Arg
            100                 105                 110

Ser Pro Pro Gly Lys Pro Gln Gly Pro Pro Gln Gly Gly Asn Gln
            115                 120                 125

Pro Gln Gly Pro Pro Pro Pro Gly Lys Pro Gln Gly Pro Pro Pro
    130                 135                 140

Gln Gly Gly Asn Lys Pro Gln Gly Pro Pro Pro Gly Lys Pro Gln
145                 150                 155                 160

Gly Pro Pro Pro Gln Gly Asp Asn Lys Ser Arg Ser Ser Arg Ser Pro
                165                 170                 175

Pro Gly Lys Pro Gln Gly Pro Pro Gln Gly Gly Asn Gln Pro Gln
            180                 185                 190

Gly Pro Pro Pro Pro Gly Lys Pro Gln Gly Pro Pro Gln Gly
        195                 200                 205
```

-continued

```
Gly Asn Lys Pro Gln Gly Pro Pro Pro Gly Lys Pro Gln Gly Pro
    210                 215                 220

Pro Pro Gln Gly Asp Asn Lys Ser Gln Ser Ala Arg Ser Pro Pro Gly
225             230                 235                 240

Lys Pro Gln Gly Pro Pro Pro Gln Gly Gly Asn Gln Pro Gln Gly Pro
            245                 250                 255

Pro Pro Pro Pro Gly Lys Pro Gln Gly Pro Pro Pro Gln Gly Gly Asn
        260                 265                 270

Lys Ser Gln Gly Pro Pro Pro Pro Gly Lys Pro Gln Gly Pro Pro Pro
        275                 280                 285

Gln Gly Gly Ser Lys Ser Arg Ser Ser Arg Ser Pro Pro Gly Lys Pro
    290                 295                 300

Gln Gly Pro Pro Pro Gln Gly Gly Asn Gln Pro Gln Gly Pro Pro Pro
305             310                 315                 320

Pro Pro Gly Lys Pro Gln Gly Pro Pro Pro Gln Gly Gly Asn Lys Pro
            325                 330                 335

Gln Gly Pro Pro Pro Pro Gly Lys Pro Gln Gly Pro Pro Pro Gln Gly
            340                 345                 350

Gly Ser Lys Ser Arg Ser Ala Arg Ser Pro Pro Gly Lys Pro Gln Gly
        355                 360                 365

Pro Pro Gln Gln Glu Gly Asn Asn Pro Gln Gly Pro Pro Pro Pro Ala
    370                 375                 380

Gly Gly Asn Pro Gln Gln Pro Gln Ala Pro Pro Ala Gly Gln Pro Gln
385             390                 395                 400

Gly Pro Pro Arg Pro Pro Gln Gly Gly Arg Pro Ser Arg Pro Pro Gln
            405                 410                 415
```